(12) United States Patent
Addison et al.

(10) Patent No.: US 7,035,679 B2
(45) Date of Patent: Apr. 25, 2006

(54) WAVELET-BASED ANALYSIS OF PULSE OXIMETRY SIGNALS

(75) Inventors: Paul Stanley Addison, Edinburgh (GB); James Nicholas Watson, Edinburgh (GB)

(73) Assignee: Cardiodigital Limited, Elvingston, Gladsmuir (GB)

( * ) Notice: Subject to any disclaimer, the term of this patent is extended or adjusted under 35 U.S.C. 154(b) by 65 days.

(21) Appl. No.: 10/480,983

(22) PCT Filed: Jun. 21, 2002

(86) PCT No.: PCT/GB02/02843

§ 371 (c)(1),
(2), (4) Date: Dec. 16, 2003

(87) PCT Pub. No.: WO03/000125

PCT Pub. Date: Jan. 3, 2003

(65) Prior Publication Data

US 2005/0070774 A1    Mar. 31, 2005

(51) Int. Cl.
*A61B 5/00* (2006.01)

(52) U.S. Cl. .................................. 600/323; 600/529

(58) Field of Classification Search .......... 600/323–24, 600/324, 330, 310, 322, 336, 529
See application file for complete search history.

(56) References Cited

U.S. PATENT DOCUMENTS

| 5,385,144 | A | * | 1/1995 | Yamanishi et al. | ......... 600/330 |
| 5,830,137 | A | * | 11/1998 | Scharf | ................. 600/323 |
| 6,011,985 | A | | 1/2000 | Athan et al. | |
| 6,117,075 | A | | 9/2000 | Barnea | |
| 6,135,966 | A | | 10/2000 | Ko | |
| 6,208,951 | B1 | | 3/2001 | Kumar et al. | |
| 6,352,502 | B1 | * | 3/2002 | Chaiken et al. | ............. 600/473 |
| 6,519,486 | B1 | * | 2/2003 | Edgar et al. | ................ 600/336 |

FOREIGN PATENT DOCUMENTS

| WO | WO 00/77675 A1 | * | 12/2000 |
| WO | WO01/25802 A2 | | 4/2001 |
| WO | WO01/82099 A1 | | 11/2001 |

* cited by examiner

*Primary Examiner*—Eric F. Winakur
(74) *Attorney, Agent, or Firm*—Drinker Biddle & Reath LLP

(57) ABSTRACT

A pulse oximetry signal, suitably a photoplethysmogram (PPG), is decomposed by wavelet transform techniques, and the decomposed signal analysed to provide selected physiological data. The signal may be processed to remove noise, artefacts, or transient features. Information on respiration may also be recovered.

35 Claims, 27 Drawing Sheets

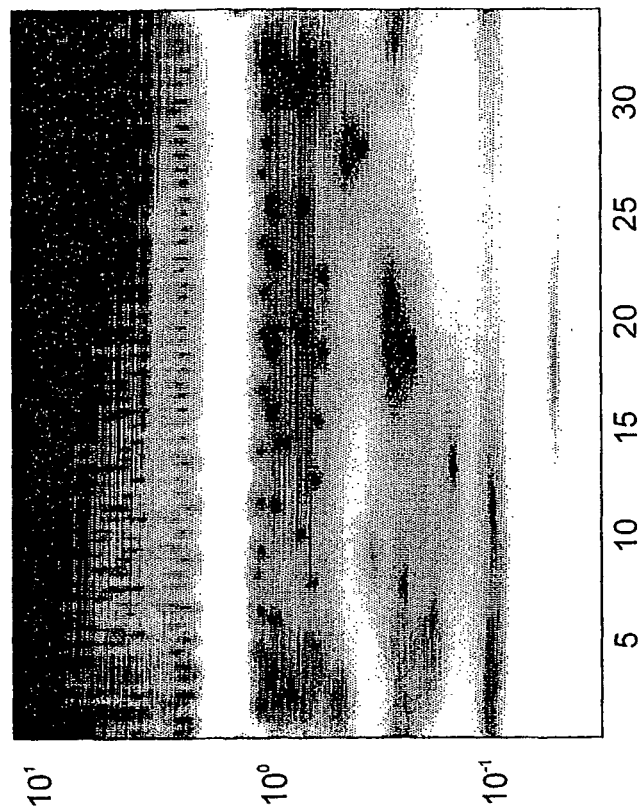
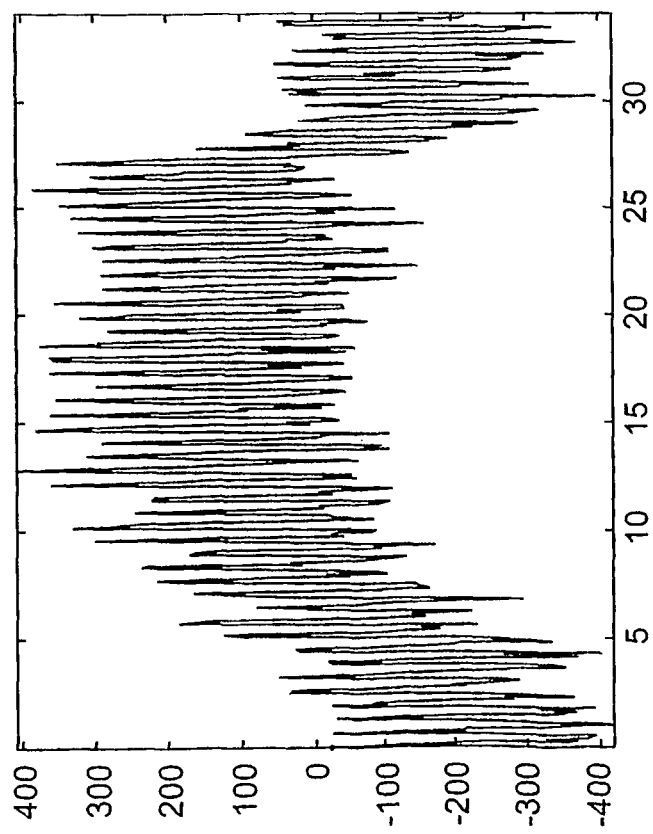
Fig. 6b
Fig. 6a

Legend:

'o' - healthy controls.
'+' - children attending the accident and emergency department

WAVELET-BASED ANALYSIS OF PULSE OXIMETRY SIGNALS

FIELD OF THE INVENTION

The present invention relates to a method of analysis of medical signals, and in particular to a method of decomposition of signals used in pulse oximetry. Specifically the invention relates to an improved method of denoising such signals and in the extraction of clinically useful information from such signals including the monitoring and analysis of patient respiration.

BACKGROUND

Oximetry is an optical method for measuring oxygenated haemoglobin in blood. Oximetry is based on the ability of different forms of haemoglobin to absorb light of different wavelengths oxygenated haemoglobin ($HbO_2$) absorbs light in the red spectrum and deoxygenated or reduced haemoglobin (RHb) absorbs light in the near-infrared spectrum. When red and infrared light is passed through a blood vessel the transmission of each wavelength is inversely proportional to the concentration of $HbO_2$ and RHb in the blood.

Pulse oximeters can differentiate the alternating light input from arterial pulsing from the constant level contribution of the veins and other non-pulsatile elements. Only the alternating light input is selected for analysis. Pulse oximetry has been shown to be a highly accurate technique.

Figure 1A:
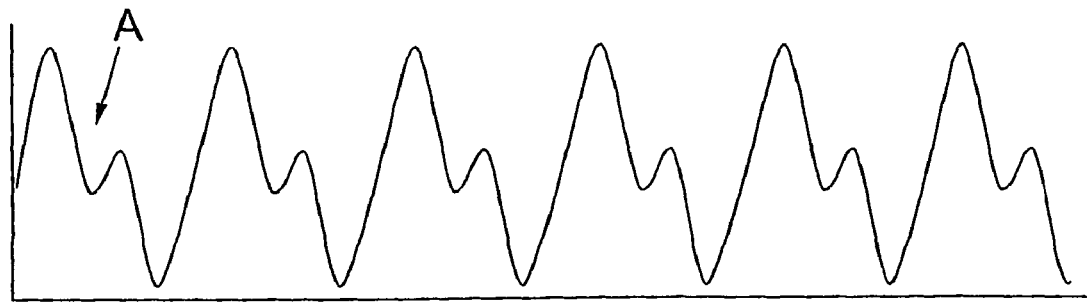
Figure 1B:

The contemporary pulse oximeter unit normally provides three outputs:
1. the arterial oxygen saturation
2. the heart rate
3. a fluctuating time series—the pulse oximeter trace or plethysmographic waveform The normal pulse oximeter waveform—the photoplethysmogram (PPG)—bears a strong resemblance to an arterial pressure waveform complete with dichrotic notch. A schematic of a typical pulse oximeter trace from a finger probe is shown in FIG. 1a. The repeating double humped (with a notch A in-between) nature of the waveform is evident in the plot. Often, the second hump disappears and a signal such as that in FIG. 1b is obtained. This may indicate a clinical condition such as reduced arterial compliance. Often, for this type of signal, there is a marked change in the gradient of the falling waveform (i.e. a kink) as indicated by the arrow B in the plot.

Figure 2:
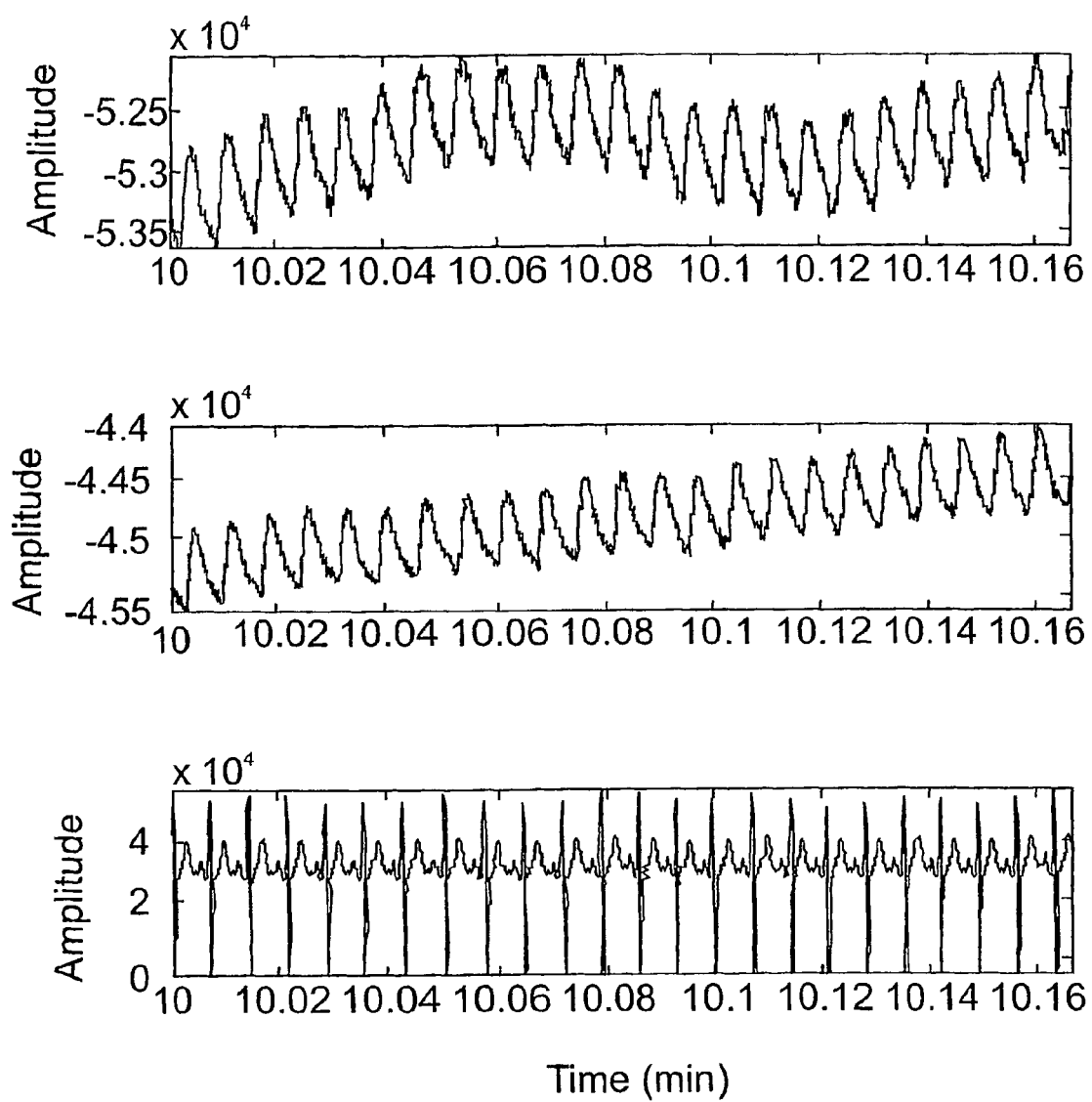

FIG. 2 contains a plot of three simultaneously acquired signals acquired from a patient. These are: a finger pulse oximetry trace, an ear pulse oximetry trace and an ECG. These 10 second segments have been cut from a much longer signal. Note the significant drift associated with the pulse oximetry traces.

SUMMARY OF THE INVENTION

The invention provides a method of measuring physiological parameters, as defined in claim 1, and also provides a method of processing a pulse oximetry signal, as defined in claim 2.

From another aspect, the invention provides a physiological measurement system as defined in claim 22.

Preferred features and advantages of the invention will be apparent from the other claims and from the following description.

The invention in its preferred forms provides a method for the decomposition of pulse oximetry signals using wavelet transforms which allows for underlying characteristics which are of clinical use to be displayed and measured. The method utilises wavelet transforms to decompose the signal in wavelet space. The wavelet decomposition of one or more or a combination of signals can then be used to:

(a) construct a wavelet visualisation of the signal—the preferred method being that which uses wavelet energy surfaces plotted against the location parameter b and the inverse of the dilation parameter a. This visualisation would highlight salient information in a more useful form for clinical diagnosis (e.g. see 2D and 3D scalograms in figures described below). This form of information presentation should facilitate the interpretation of such signals. It is envisaged that the clinician would be provided with a real time display of the scalogram.

(b) provide, through the position and amplitude of features in the scalogram, measurable characteristics of the signal for estimation of the health of the monitored patient. These characteristics may include wavelet-based parameters, including ratios, for the determination of oxygen saturation. This is important for the determination of the correct therapy for the patient.

(c) provide, using information derived from the wavelet transform (i.e. from the transform, scalogram (energy density) normalised scalogram, wavelet power spectrum, modulus maxima, wavelet ridges, phase representation, etc.) a method for measuring the cardiovascular system compliance.

(d) provide, using information derived from the wavelet transform (i.e. from the transform, scalogram (energy density) normalised scalogram, wavelet power spectrum, modulus maxima, wavelet ridges, phase representation, etc.) a method for detecting the presence and location of pertinent features (e.g. maxima, minima, notch, kink, etc.) and timescales within the pulse oximetry signal and use of this information for a clinically useful purpose.

(e) provide, using information derived from the wavelet transform (i.e. from the transform, scalogram (energy density) normalised scalogram, wavelet power spectrum, modulus maxima, wavelet ridges, phase representation, etc.) a method for identifying features of the wavelet power spectrum which can be used as clinical markers of the health of the patient at the time of data collection (f) provide, using information derived from the wavelet transform (i.e. from the transform, scalogram (energy density) normalised scalogram, wavelet power spectrum, modulus maxima, wavelet ridges, phase representation, etc.) a method for identifying features which can be used as clinical markers of the future health of the patient, that is as markers of the subsequent deterioration or improvement of the health of the patient. These markers will be incorporated within a prediction algorithm.

(g) provide, using information derived from the wavelet transform (i.e. from the transform, scalogram (energy density) normalised scalogram, wavelet power spectrum, modulus maxima, wavelet ridges, phase representation, etc.) a method for detecting and monitoring the patient breathing signal. This method would be suitable for the monitoring the regularity of the breathing pattern and patient breathing rate where high levels of noise and erroneous artefact affects the signal. This information to be used in conjunction with other relevant clinical information for clinically useful purposes.

(h) provide, using information derived from the wavelet transform (i.e. from the transform, scalogram (energy density) normalised scalogram, wavelet power spectrum, modulus maxima, wavelet ridges, phase representation, etc.) an accurate method for detecting and monitoring the patient breathing rate. This information to be displayed on the pulse oximeter device. This information to be used in conjunction with other relevant clinical information for clinically useful purposes.

(i) provide a method for the disassociation of artefact from the pertinent signal components, where artefact includes noise, coherent signal, movement artefact and if required breathing artefact. The preferred method of performing this would be a modulus maxima technique.

(j) provide a method for the classification of the current status of the patient's health based on the wavelet transform features and incorporating a suitable classification method. The optimal combination of features will be employed. The classification methods may include non-parametric Bayesian classification methods, neural networks, etc. and also include preprocessing discriminant analysis techniques such as principle component analysis and/or linear discriminant analysis for reducing the dimensionality of multidimensional data.

(k) provide a method for the prediction of the future status of the patient's health based on the wavelet transform features and incorporating a suitable classification method. The optimal combination of features will be employed. The classification methods may include non-parametric Bayesian classification methods, neural networks, etc. and also include preprocessing discriminant analysis techniques such as principle component analysis and/or linear discriminant analysis for reducing the dimensionality of multidimensional data.

Embodiments of the invention will now be described, by way of example only, with reference to the drawings:

FIG. 1(a): Arterial Pulse and Pulse Oximetry Signal, as discussed above.

FIG. 1(b) Arterial Pulse and Pulse Oximetry Signal, as discussed above.

FIG. 2: The Three Collected traces: Top—Ear pulse oximetry signal, Middle—Finger pulse oximetry signal, Lower—ECG.

Figures 3A, 3D:
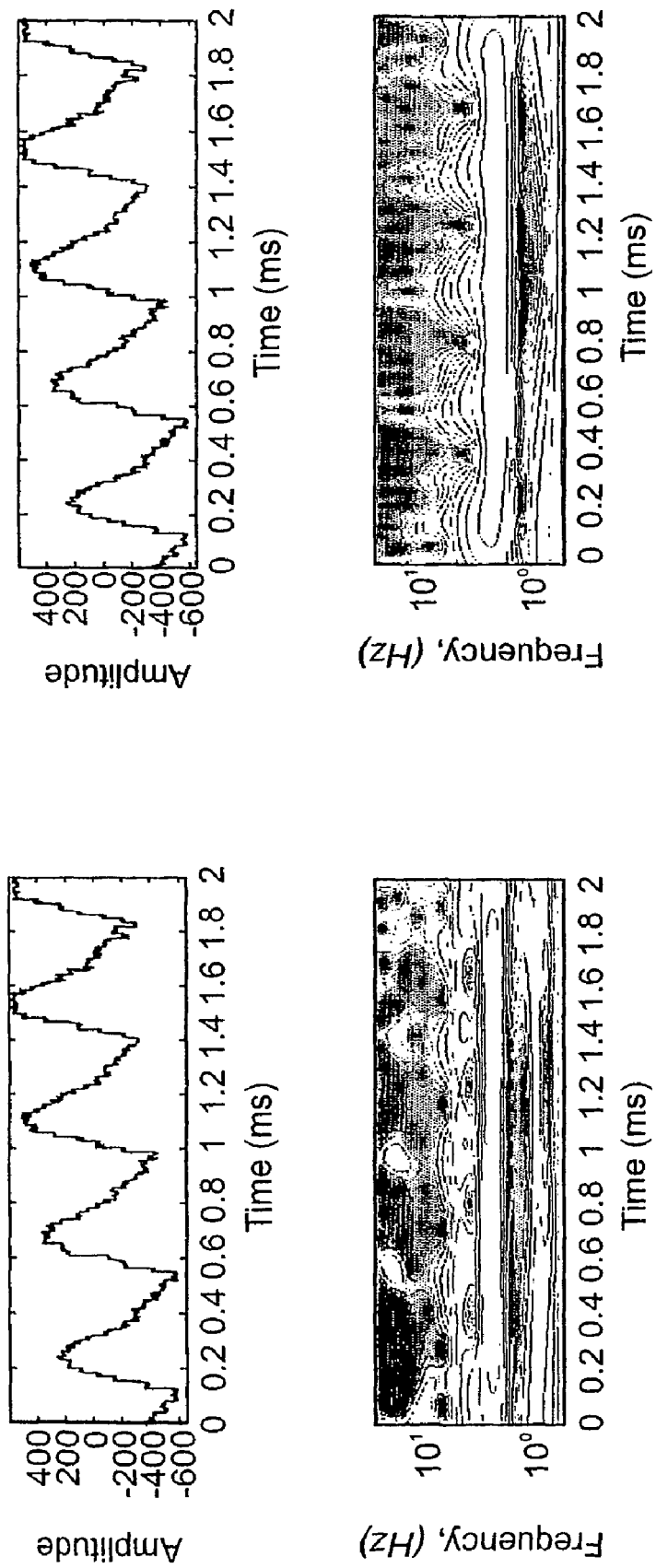
Figure 3E:
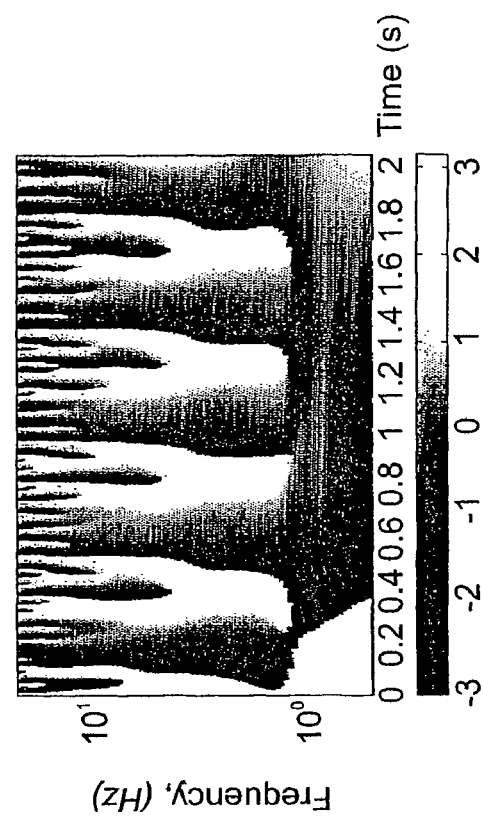
Figure 3B:
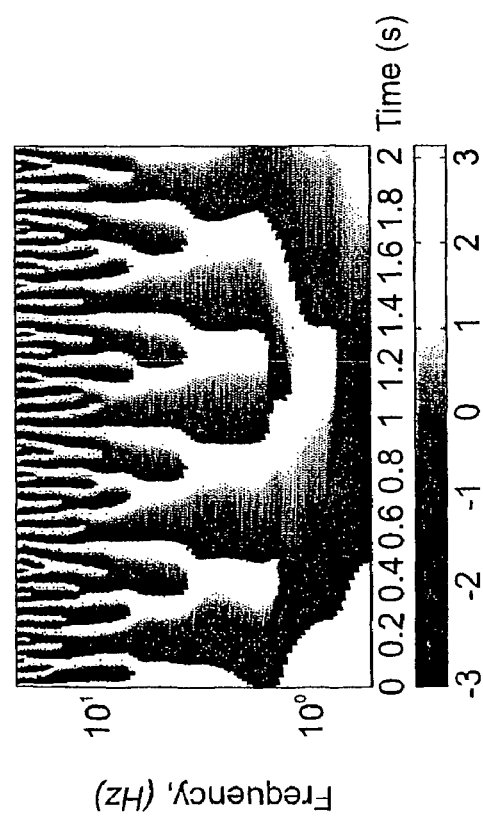
Figures 3C, 3F:
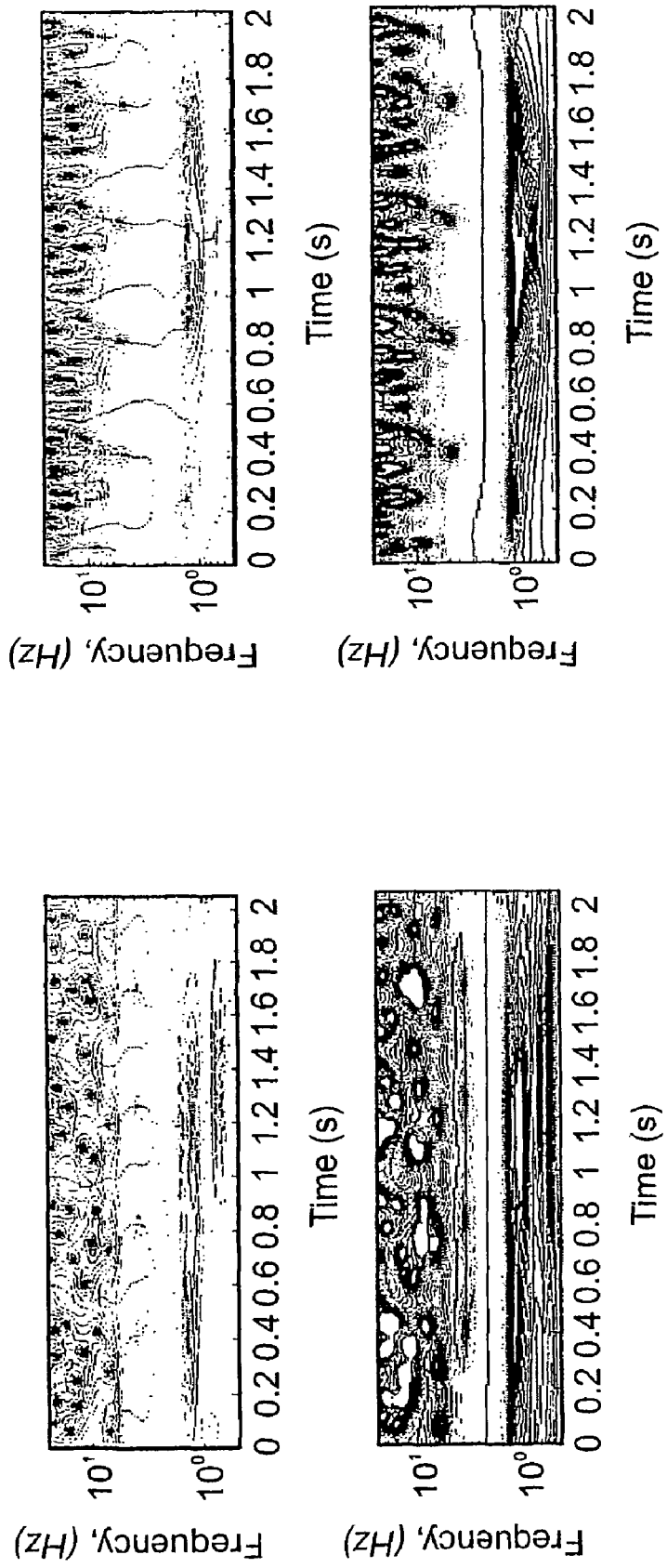
Figure 4D:
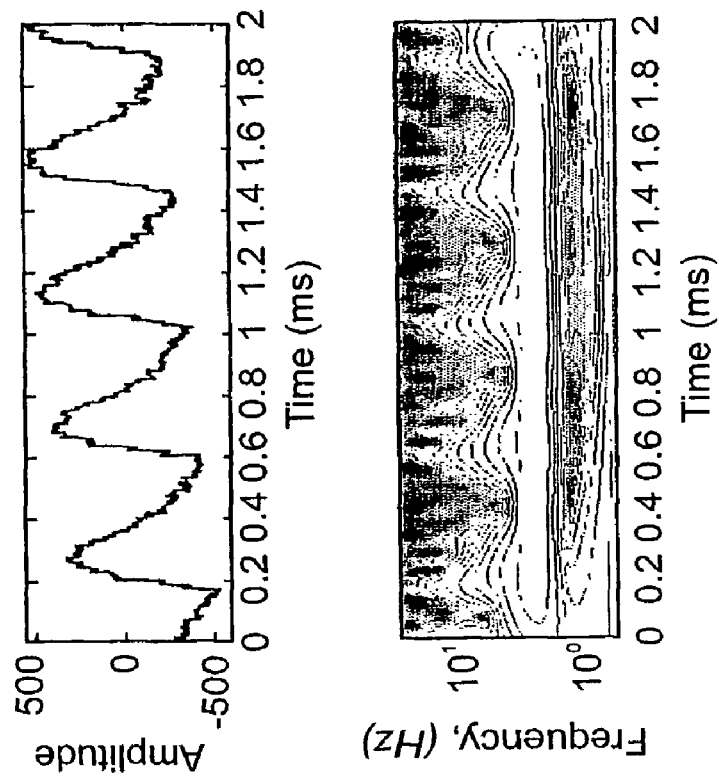
Figure 4A:
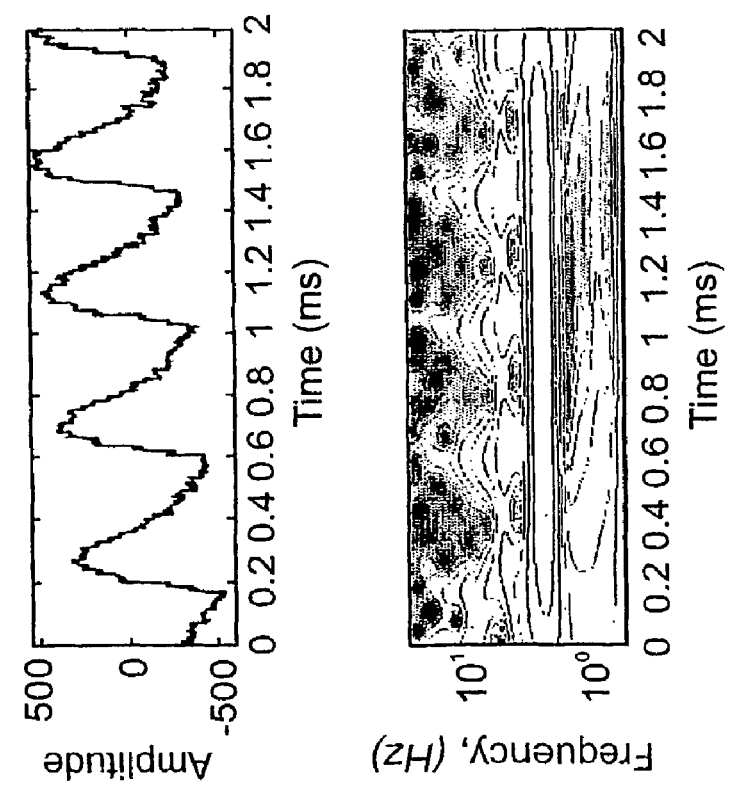
Figure 4E:
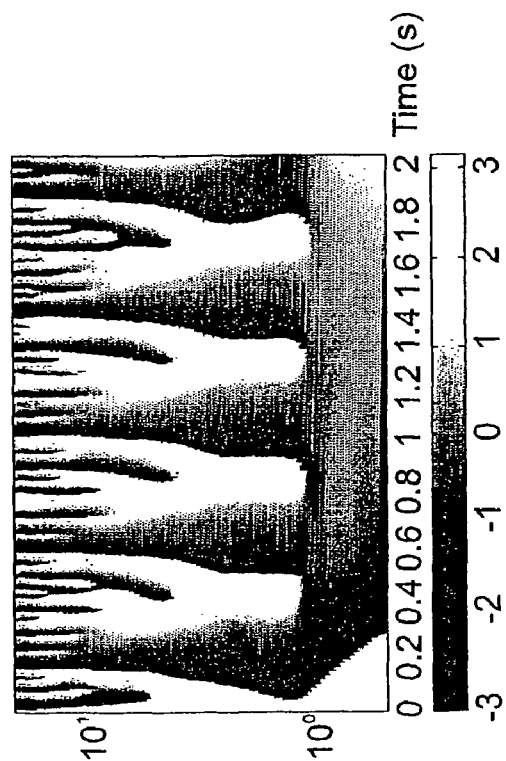
Figure 4B:
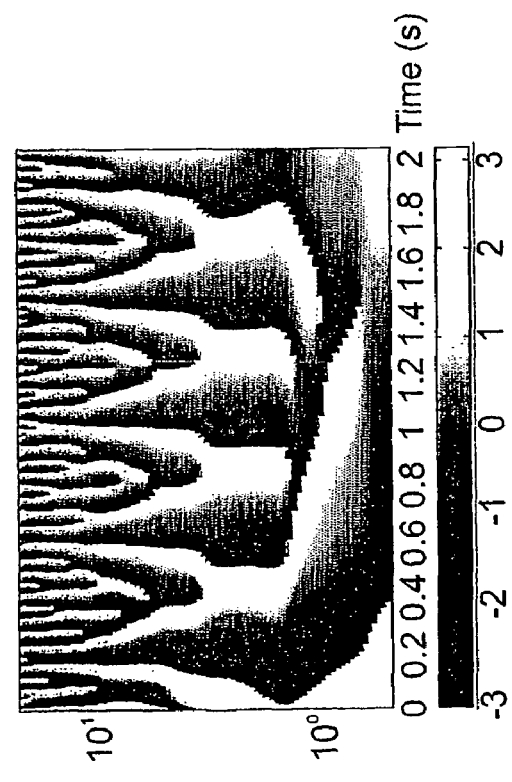
Figure 4F:
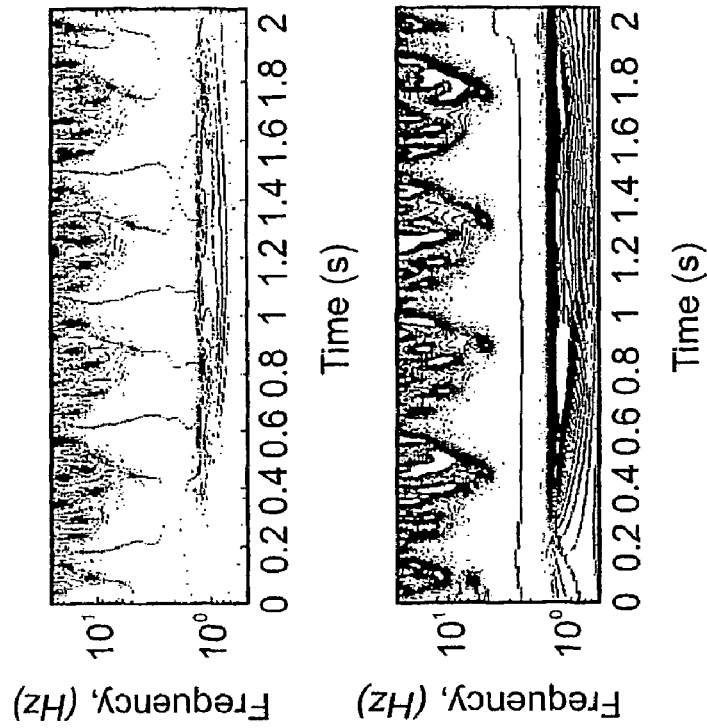
Figure 4C:
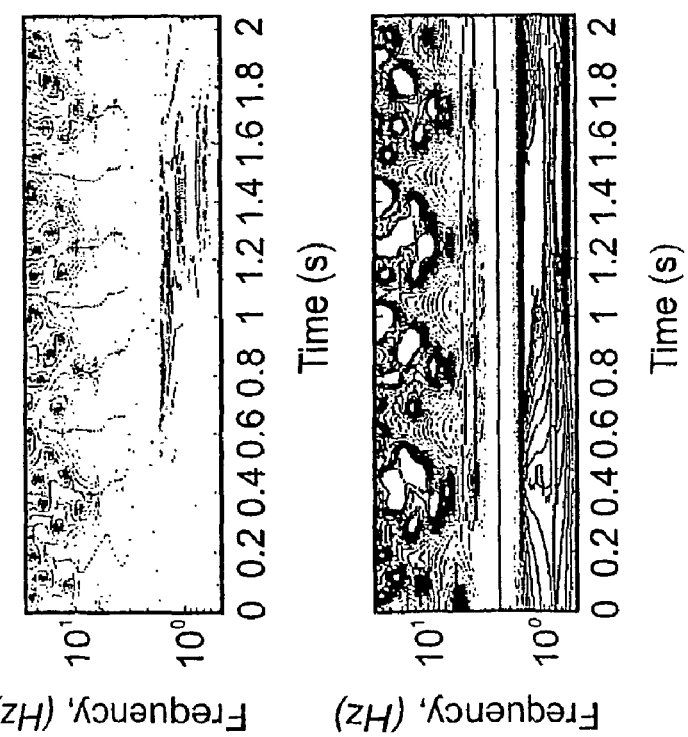

FIG. 3(a): Wavelet analysis of a 2 second segment of pulse oximetry signal taken from the ear 10 minutes into the recording. Top: the pulse oximetry trace. Bottom: the scalogram. Standard Morlet wavelet with $\omega_0=5.5$ FIG. 3(b): Wavelet analysis of a 2 second segment of pulse oximetry signal taken from the ear 10 minutes into the recording. The Phase plot. Standard Morlet wavelet with $\omega_0=5.5$ FIG. 3(c): Wavelet analysis of a 2 second segment of pulse oximetry signal taken from the ear 10 minutes into the recording. Top: the modulus maxima plot. Bottom: the ridge plot. Standard Morlet wavelet with $\omega_0=5.5$ FIG. 3(d): Wavelet analysis of a 2 second segment of pulse oximetry signal taken from the ear 10 minutes into the recording. Top: the pulse oximetry trace. Bottom: the scalogram. Complete Morlet wavelet with $\omega_0=3$ FIG. 3(e): Wavelet analysis of a 2 second segment of pulse oximetry signal taken from the ear 10 minutes into the recording. The Phase plot. Complete Morlet wavelet with $\omega_0=3$ FIG. 3(f): Wavelet analysis of a 2 second segment of pulse oximetry signal taken from the ear 10 minutes into the recording. Top: the modulus maxima plot. Bottom: the ridge plot. Complete Morlet wavelet with $\omega_0=3$ FIG. 4(a): Wavelet analysis of a 2 second segment of pulse oximetry signal taken from the finger 10 minutes into the recording. Top: the pulse oximetry trace. Bottom: the scalogram. Standard Morlet wavelet with $\omega_0=5.5$ FIG. 4(b): Wavelet analysis of a 2 second segment of pulse oximetry signal taken from the finger 10 minutes into the recording. The Phase plot. Standard Morlet wavelet with $\omega_0=5.5$ FIG. 4(c): Wavelet analysis of a 2 second segment of pulse oximetry signal taken from the finger 10 minutes into the recording. Top: the modulus maxima plot. Bottom: the ridge plot. Standard Morlet wavelet with $\omega_0=5.5$ FIG. 4(d): Wavelet analysis of a 2 second segment of pulse oximetry signal taken from the finger 10 minutes into the recording. Top: the pulse oximetry trace. Bottom: the scalogram. Complete Morlet wavelet with $\omega_0=3$ FIG. 4(e): Wavelet analysis of a 2 second segment of pulse oximetry signal taken from the finger 10 minutes into the recording. The Phase plot. Complete Morlet wavelet with $\omega_0=3$ FIG. 4(f): Wavelet analysis of a 2 second segment of pulse oximetry signal taken from the finger 10 minutes into the recording. Top: the modulus maxima plot. Bottom: the ridge plot. Complete Morlet wavelet with $\omega_0=3$ FIG. 5: Region Segmentation in Phase Space FIG. 6(a): Wavelet Denoising and Detrending. Morlet Wavelet $\omega_0=5.5$. Original Signal.

Figure 6D:
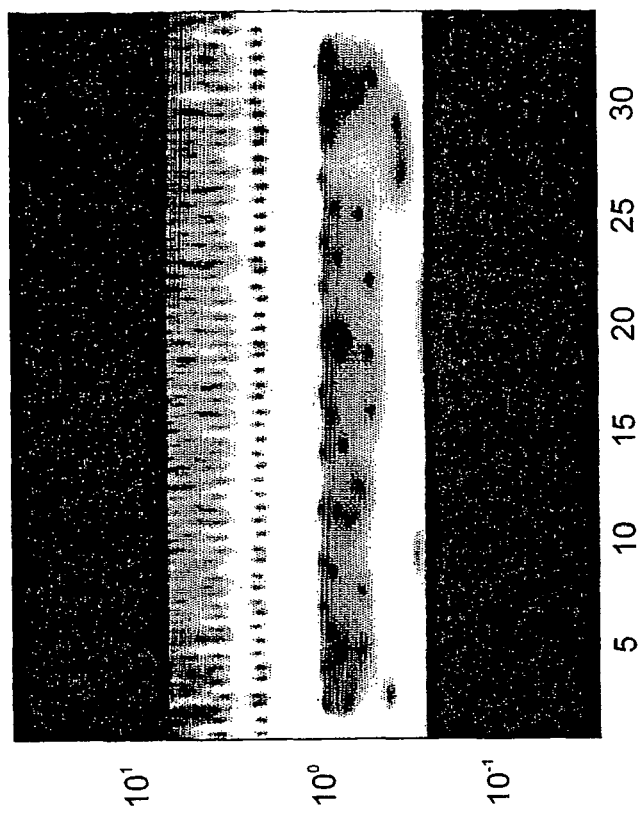
Figure 6C:
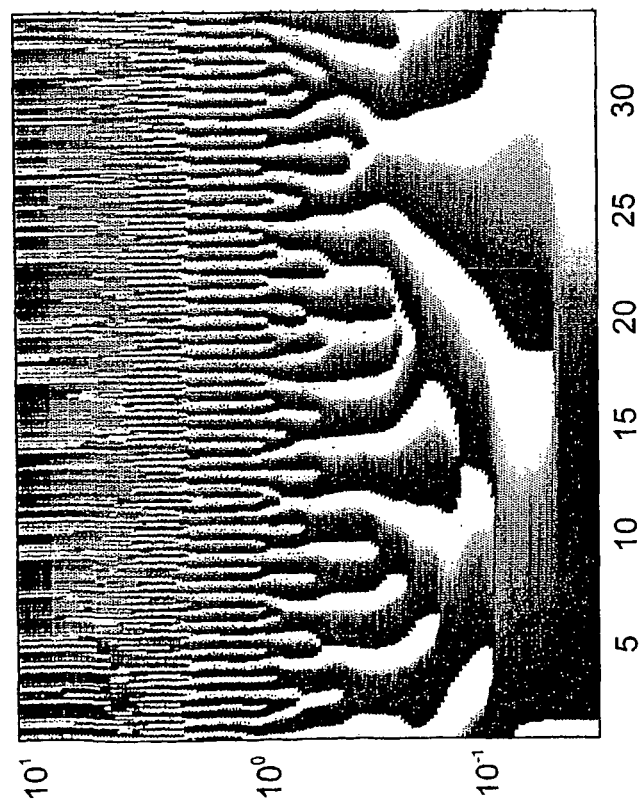

FIG. 6(b): Wavelet Denoising and Detrending. Morlet Wavelet $\omega_0=5.5$. Scalogram FIG. 6(c): Wavelet Denoising and Detrending. Morlet Wavelet $\omega_0=5.5$. Phase Plot FIG. 6(d): Wavelet Denoising and Detrending. Morlet Wavelet $\omega_0=5.5$. Cropped Scalogram FIG. 6(e): Wavelet Denoising and Detrending. Morlet Wavelet $\omega_0=5.5$. The original trace (top); the reconstructed trace (middle); the denoised and detrended trace (bottom).

Figure 7B:
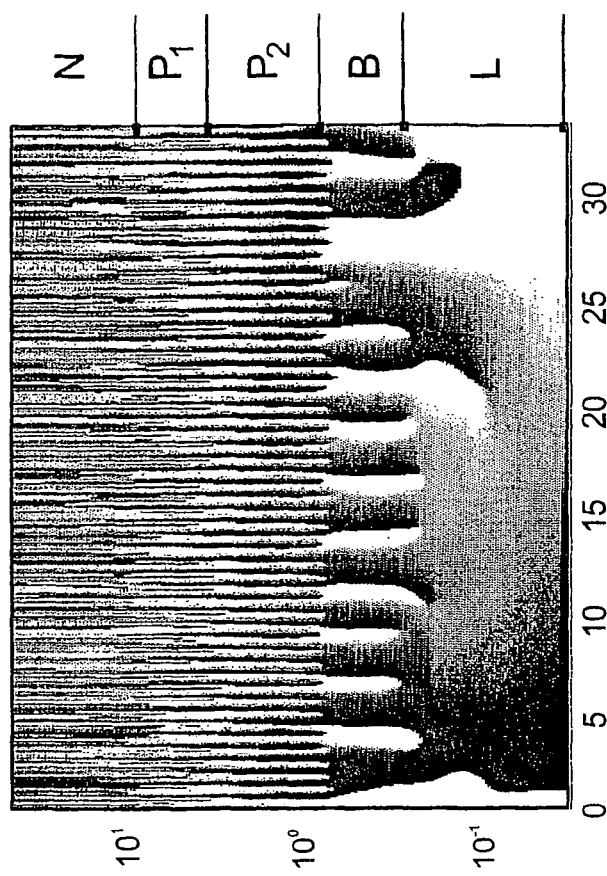
Figure 7A:
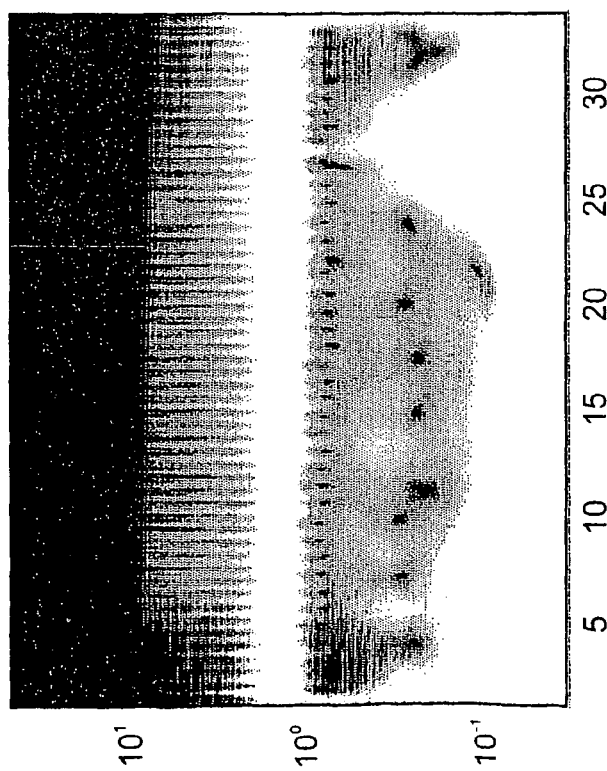

FIG. 7(a): Wavelet Denoising and Detrending. Morlet Wavelet $\omega_0=2$. Original Signal.

Figure 7C:
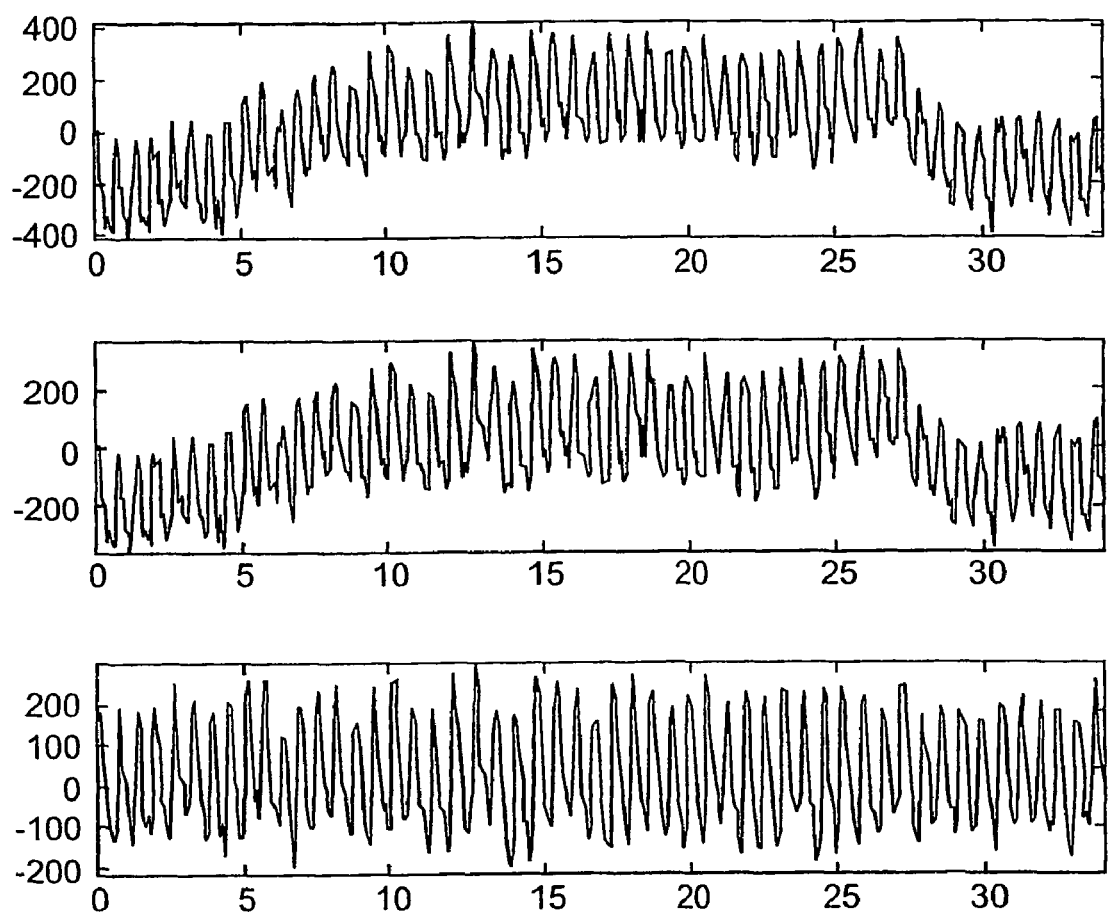
Figure 7D:
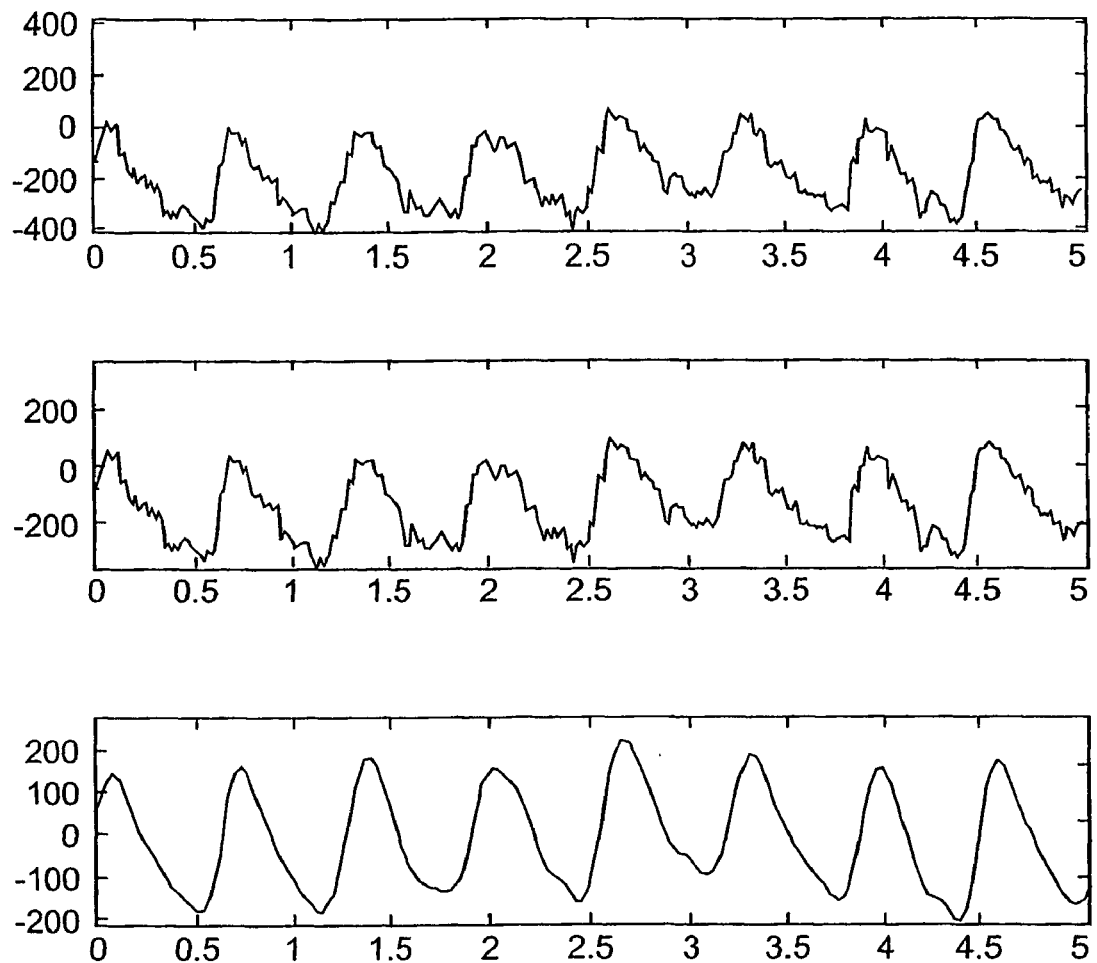

FIG. 7(b): Wavelet Denoising and Detrending. Morlet Wavelet $\omega_0=2$. Phase Plot FIG. 7(c): Wavelet Denoising and Detrending. Morlet Wavelet $\omega_0=2$. Original and reconstructed signals FIG. 7(d): Wavelet Denoising and Detrending. Morlet Wavelet $\omega_0=2$. Blow up of FIG. 7(c)

Figure 7E:
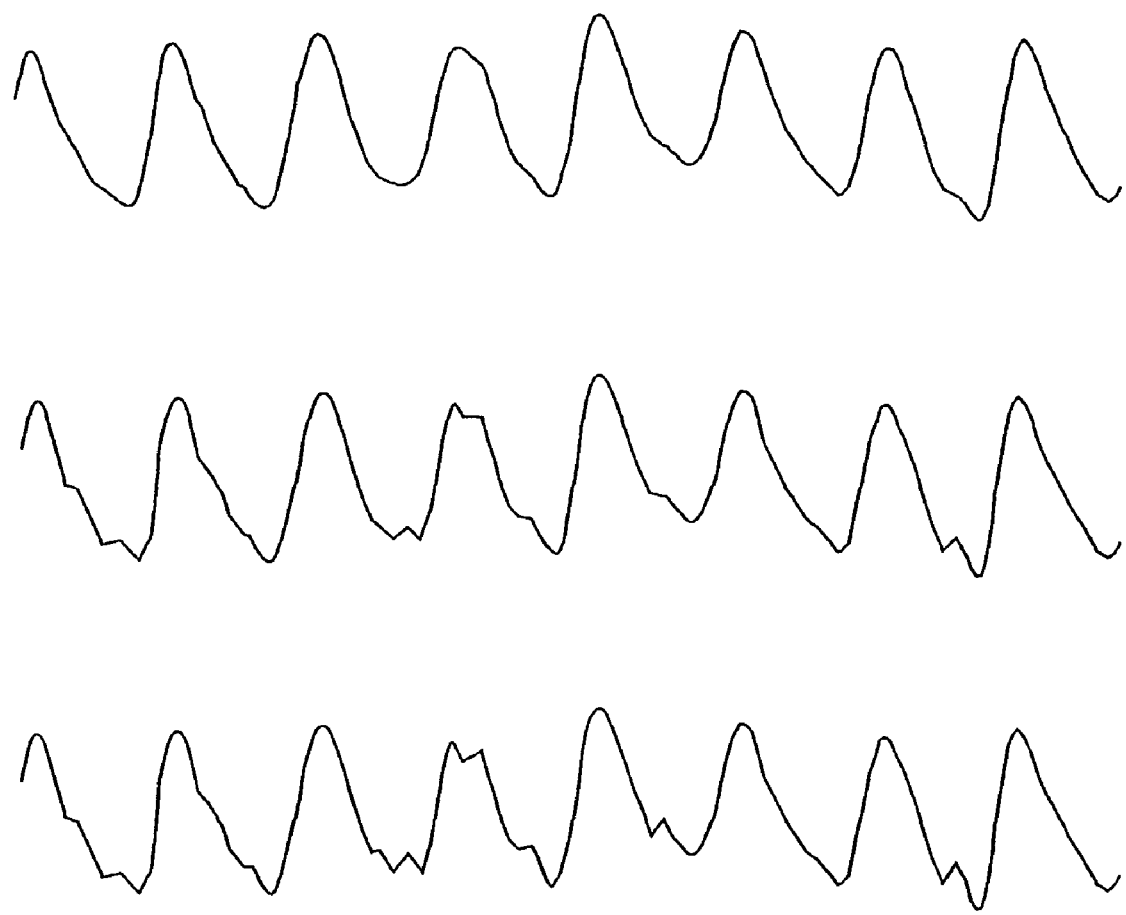

FIG. 7(e): Wavelet Denoising and Detrending. Morlet Wavelet $\omega_0=2$. Three different high frequency cut-off thresholds—increasing from top to bottom.

Figure 8A:
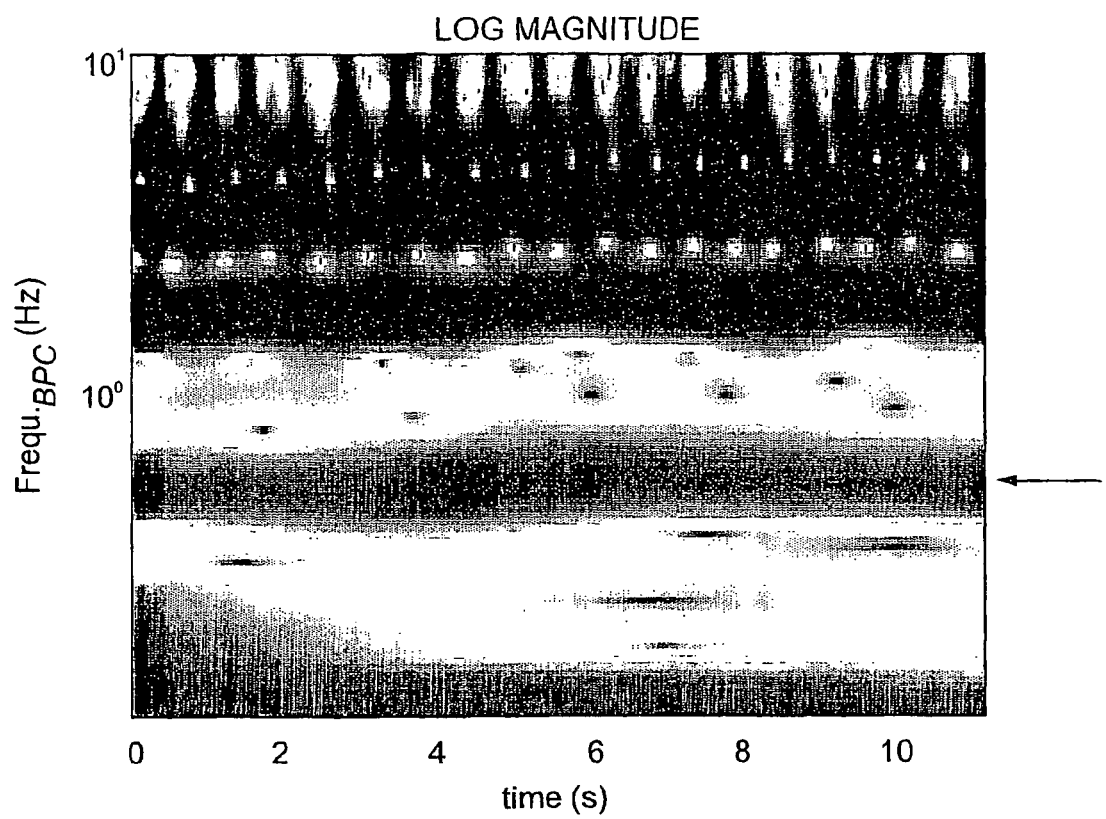

FIG. 8(a): Scalogram showing the breathing ridge

Figure 8B:
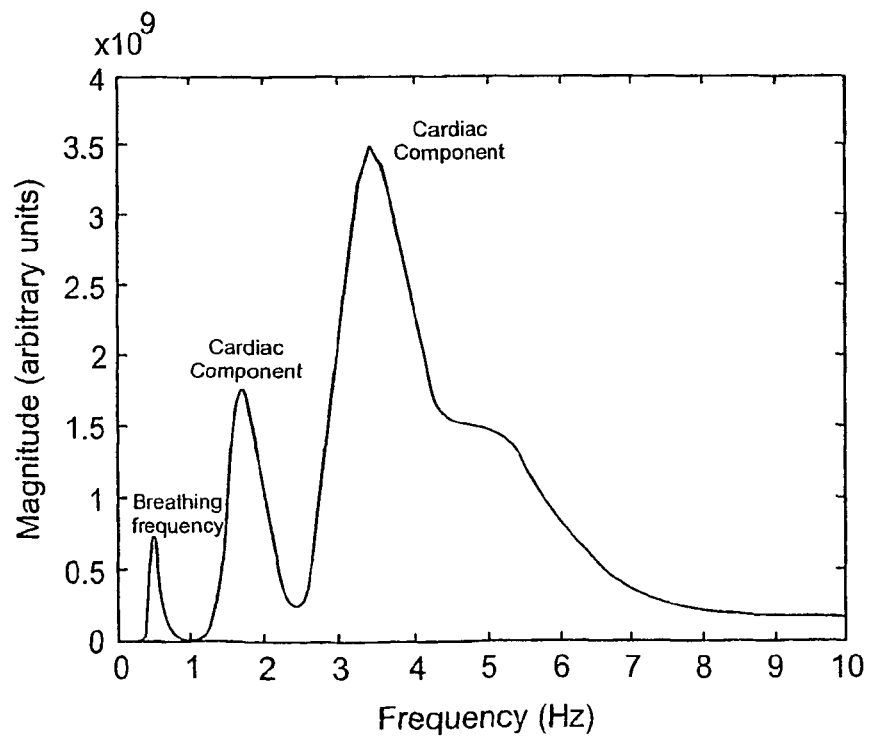

FIG. 8(b): A Collapsed Scalogram showing the breathing and heart rates.

Figure 9A:
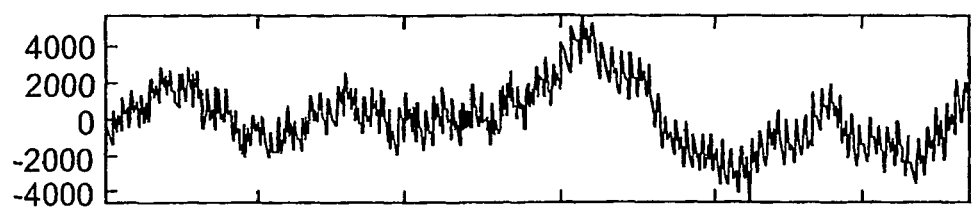

FIG. 9(a): The Analysis of a Plethysmogram Breathing Experiment Sub-Study:Pulse oximeter trace.

Figure 9B:
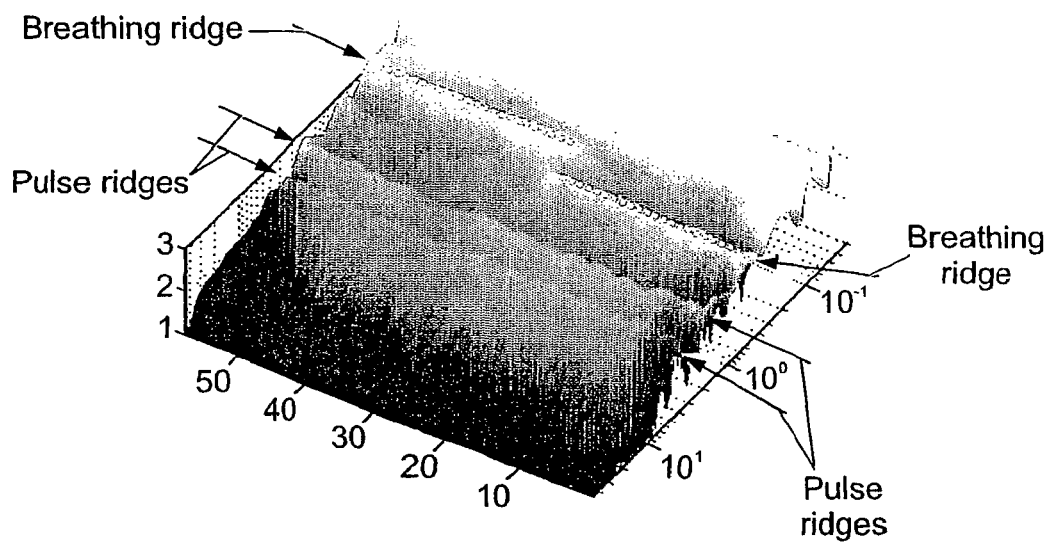

FIG. 9(b): The Analysis of a Plethysmogram Breathing Experiment Sub-Study: The Modulus of the trace in FIG. 9(a) showing ridges associated with pulse and breathing.

Figure 9C:
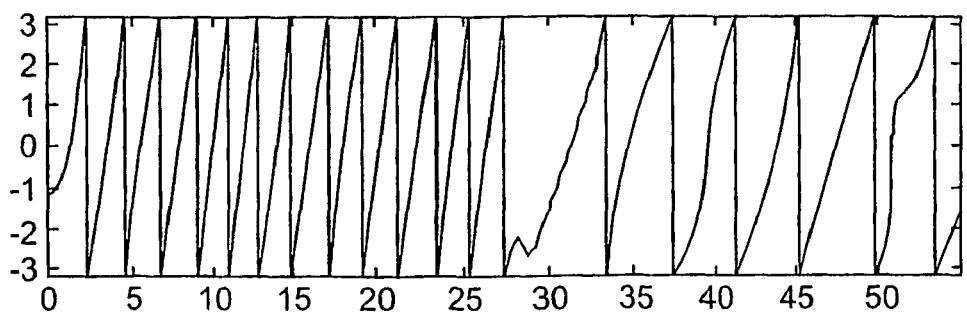

FIG. 9(c): The Analysis of a Plethysmogram Breathing Experiment Sub-Study: the phase associated with the breathing ridges in FIG. 9(b).

Figure 10A:
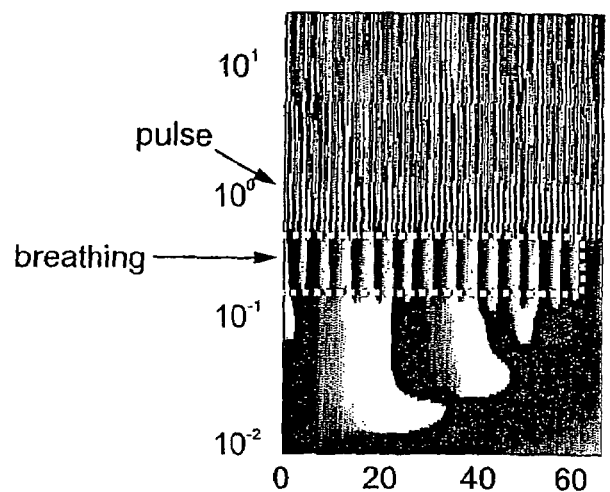

FIG. 10(a): Phase following of respiration

FIG. 10(*b*): Showing the steps of constant phase minima across scales.

FIG. 11(*a*): Frequency Modulation of the dominant cardiac frequency bands

FIG. 11(*b*): Amplitude Modulation of the dominant cardiac frequency bands

FIG. 11(*c*): Individual Breathing features resolved using a low oscillation wavelet (One such feature indicated by arrow.)

Figure 12:
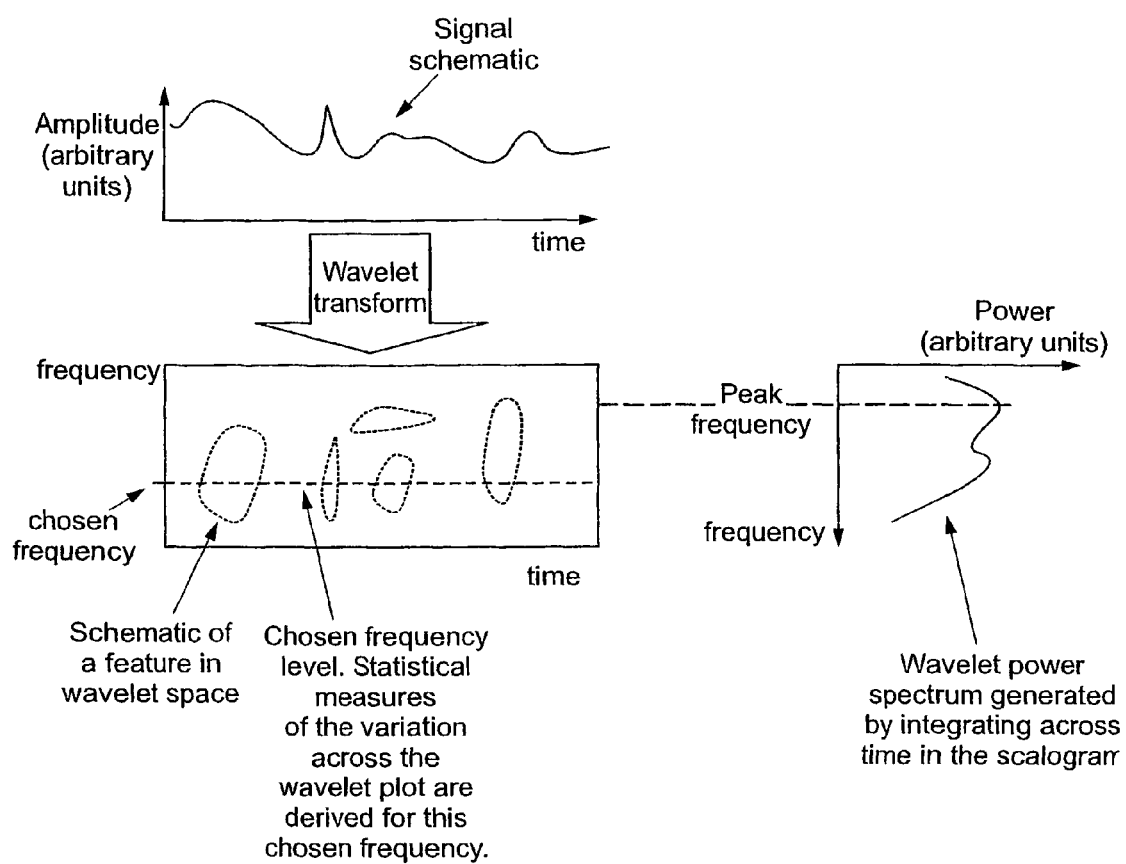

FIG. 12: A schematic diagram of the signal, its transformation as a scalogram, the associated wavelet power spectrum.

Figure 13:
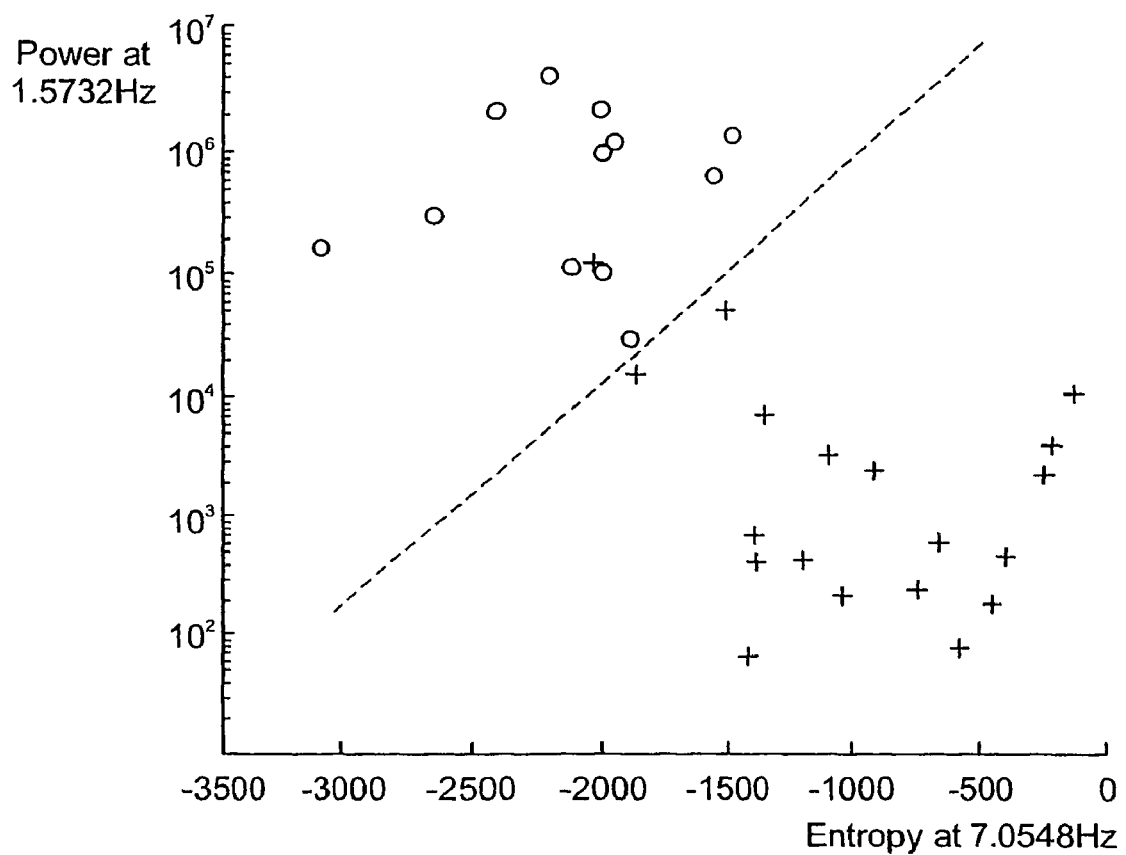

FIG. 13: Partitioning of the test data. Power is plotted against entropy at the frequency levels given. An arbitrary separation line has been plotted (dashed) in the plot.

FIG. 14(*a*): Graphical illustration of Bayesian Classification of 'ill' and 'healthy' data sets.

FIG. 14(*b*): Graphical illustration of Bayesian Classification of 'ill' and 'healthy' data sets FIG. 15: Top: PPG signal. Lower Plot: The wavelet transform modulus maxima plot corresponding to the signal.

Figure 16:
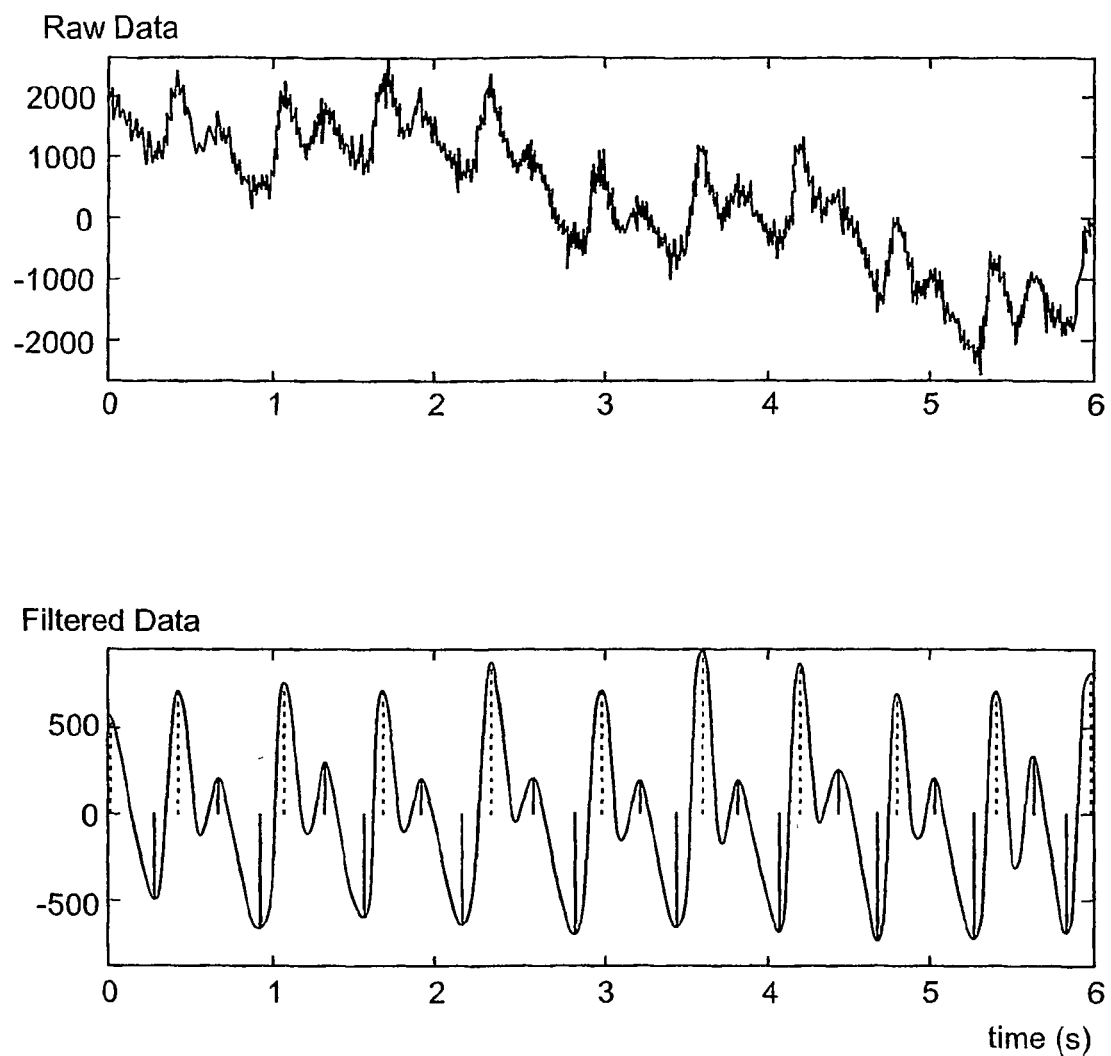

FIG. 16: Top: A raw PPG signal. Lower Plot: The wavelet transform (threshold) filtered trace with individually isolated features of the trace marked by vertical lines.

Figure 17:
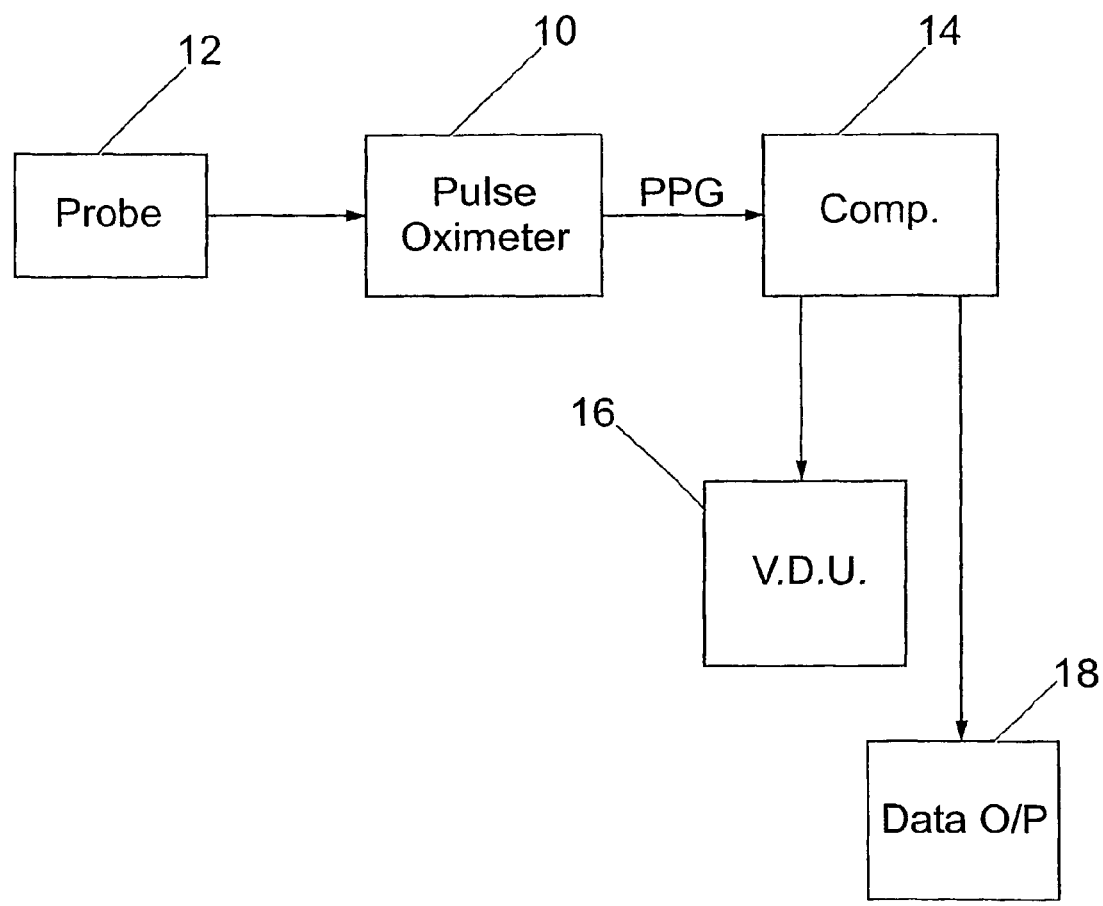

FIG. 17: A block schematic of an exemplary system for implementing the method of the invention.

THE WAVELET TRANSFORM

Wavelet transforms allow a signal to be decomposed such that both the frequency characteristics and the location of particular features in a time series may be highlighted simultaneously. This overcomes the basic shortcoming of Fourier analysis, where the spectrum only contains globally averaged information thus leading to location specific features in the signal being lost. The complete analysis of a signal requires the deduction of both the frequency make up and temporal location of the signal components. The limitation of Fourier (spectral-only) methods can be partly overcome by introducing a sliding time window which localises the analysis in time. This local or Short Time Fourier Transform (STFT) provides a degree of temporal resolution by highlighting changes in spectral response with respect to time. However, this method is always a compromise between temporal and frequency resolution (higher frequency resolution means lower temporal resolution, and vice versa) due to the fixed window width associated with it. The nature of the wavelet transform is such that it is well suited to the analysis of signals in which a more precise time resolution is required for higher frequencies than for lower ones. By employing a variable width window, it effectively zooms in on the temporal signal when analysing higher frequencies, providing higher resolution where necessary.

The wavelet transform of a continuous real-valued time signal, x(t), with respect to the wavelet function, $\psi$, is defined as $$T(a,b) = \frac{1}{\sqrt{a}} \int_{-\infty}^{\infty} \psi^*\left(\frac{t-b}{a}\right) x(t)\, dt \quad (1)$$

where t is time, a is the dilation parameter, b is the location parameter, $\psi^*((t-b)/a)$ is the complex conjugate of the analysing wavelet used in the convolution and x(t) is the signal under investigation which, in this application, is the PPG signal obtained from the pulse oximeter. The wavelet transform can therefore be thought of as the cross-correlation of the analysed signal with a wavelet function that has been translated by a value b and dilated by a factor a.

Contemporary literature suggests two methods of wavelet analysis using either discrete or continuous transforms. The discrete wavelet transform necessitates the use of orthonormal wavelets, and dilation levels are set in the form of integer powers of two. This provides a rapid method of signal decomposition, and guarantees energy conservation and exact signal reconstruction. However, the discrete transform is limited by loss of both time and frequency resolution due to the dyadic nature of the transform. Conversely, the continuous wavelet transform does provide high resolution. Thus, proper use of wavelet analysis demands identification of the correct wavelet and transform type for the given application. The inherent redundancy in the continuous wavelet method, although computationally more intensive, increases clarity in the transform space and allows for greater temporal resolution at high dilations. For this reason we prefer to employ a continuous wavelet transform in our method. Note that in practice a discretised approximation to the continuous wavelet transform integral may be employed based on the FFT algorithm where the wavelet convolution in (1) is performed as a product in Fourier space (via the convolution theorem) hence speeding up the computation.

Any wavelet function may be used in the analysis. In the examples given here we employ complex Morlet wavelets. We define the complete Morlet wavelet as $$\psi(t) = \frac{1}{\sqrt[4]{\pi}} \left( e^{i\omega_o t} e^{-\frac{\omega_o^2}{2}} \right) e^{-\frac{t^2}{2}} \quad (2)$$

where $\omega_o$ is the central frequency of the mother wavelet, t is time, i is the complex number $(-1)^{1/2}$. The second term in the brackets is known as the correction term, as it corrects for the non-zero mean of the complex sinusoid of the first term. In practice it becomes negligible for values of $\omega_o > 5$. Most investigators concentrate on wavelet transforms with $\omega_0$ in the range 5~6, where it can be performed without the correction term since it becomes very small. In this case, the Morlet wavelet becomes $$\psi(t) = \frac{1}{\sqrt[4]{\pi}} e^{i\omega_o t} e^{-\frac{t^2}{2}} \quad (3)$$

This truncated Morlet wavelet is invariably used in the literature and often referred to as simply the Morlet wavelet. Here we use the name, 'standard Morlet wavelet', for this simplified form of equation 3 and 'complete Morlet wavelet', for the complete form given by equation 2.

Modulus maxima and ridges correspond to loci of local maxima and minima in the wavelet transform. These are useful in detecting singularities and following instantaneous frequencies. A vast amount of information is contained within the continuous wavelet transform T(a,b). This can be condensed considerably by considering only local maxima and minima of the transform. Two definitions of these maxima are commonly used in wavelet analysis practice, these are:

1—Wavelet ridges, defined as $$\frac{d(|T(a,b)|^2/a)}{da} = 0 \quad (4)$$

which are used for the determination of instantaneous frequencies and amplitudes of signal components. Notice that this definition of a ridge uses the rescaled scalogram $|T(a,b)|^2/a$ as it leads to a simpler analytical solution relating the ridge to the instantaneous frequency when a standard Morlet wavelet is employed as the analysing wavelet.

2—Wavelet modulus maxima, defined as $$\frac{d|T(a,b)|^2}{db} = 0 \quad (5)$$

are used for locating and characterising singularities in the signal. (Note that equations 4 and 5 also include inflection points with zero gradient. These can be easily removed when implementing the modulus maxima method in practice.)

In the present invention described here we use modulus maxima and ridges as defined above, however, any reasonable definition of the loci of the maxima and minima of the transform may be incorporated within the method.

DETAILS OF THE METHOD

FIGS. 3 and 4 show some results from preliminary wavelet analysis undertaken on short segments of pulse oximeter traces. FIG. 3 corresponds to an ear probe signal and FIG. 4 to a finger probe signal.

The left hand column (FIGS. 3(a),3(b),3(c), 4(a),4(b),4(c)) in each figure corresponds to the analysis performed using the standard Morlet wavelet with $\omega_0=5.5$ and the right hand column (FIGS. 3(d),3(e),3(f),4(d),4(e),4(f)) corresponds to the analysis performed using the complete Morlet wavelet with $\omega_0=3$. These $\omega_0=3$ wavelets are much better for the temporal isolation of signal features.

The scalograms in FIGS. 3(a),3(d),4(a) and 4(d) are plotted below the original signals. The $\omega_0=5.5$ plots exhibit more compactness in frequency as evidenced by the thinner horizontal high energy band corresponding to the 'beat' frequency of the pulse oximeter signal. Also evident are regular dips corresponding to the kinks in the signal. The $\omega_0=3$ plots exhibit more temporal compactness where the dominant band contains undulation peaks which correspond to the repeating temporal pattern of the signal.

The phase plots are given below the scalograms in FIGS. 3 and 4 and provide information on the local matching of the wavelet with the signal. All phase plots shown exhibit regular repeating structure. The $\omega_0=3$ phase plot is considerably less cluttered than the $\omega_0=5.5$ plot due to less oscillatory nature of the wavelet used.

The lower plots in FIGS. 3 and 4 show the modulus maxima (top) and ridges (bottom) associated with the wavelet transform. These provide information concerning the location of temporal features and the instantaneous frequency of the signal respectively. Both methods allow for pertinent information within the highly redundant continuous wavelet transform to be presented (and hence extracted) in a more compact form. This information can be used within advanced filtering and prediction algorithms.

Elements of the Signal in Wavelet Space

Figure 5:
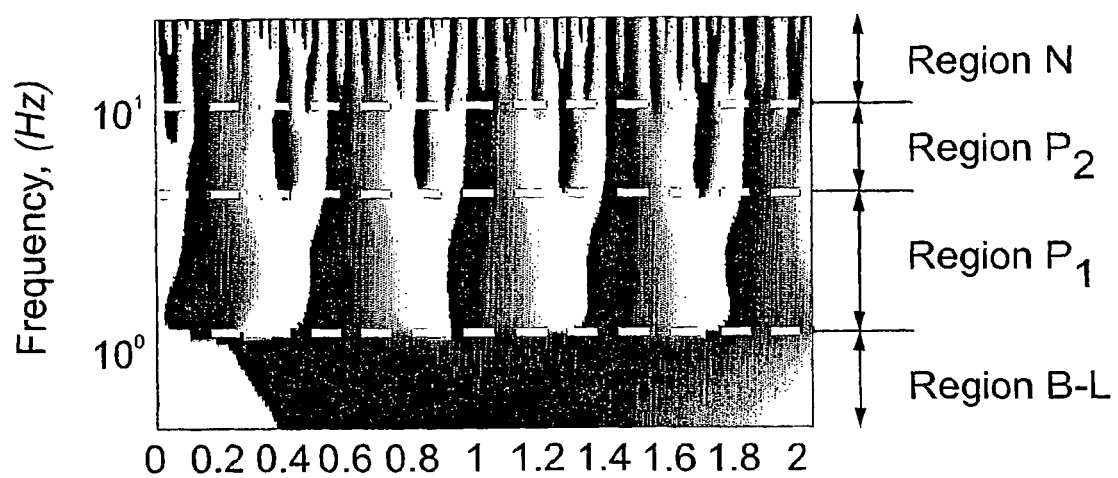

FIG. 5 contains one of the phase plots in FIG. 4 blown up and split into four distinct regions. At the very low frequency range (region B–L) there is no obvious local coherent matching of the wavelet with the signal (see below for more information concerning this region). At the next lower frequency range (region $P_1$) the phase plots exhibit a smooth repeating pattern corresponding to the regular pulsing of the signal. Above this range these undulations split into two, (region $P_2$) where the location of this new split corresponds to the marked change in slope (the kink) occurring at the decreasing part of the pulse oximeter waveform (it would correspond to the location of the notch for a double humped waveform). At the highest frequencies (region N) the phase changes become more irregular in their occurrence and correspond to the smaller fluctuations in the signal (e.g. high frequency noise, high frequency movement artefact, etc.) The features within each region could be further partitioned using advanced filtering techniques, for example incorporating wavelet modulus maxima or wavelet ridge filtering technology.

Wavelet Detrending and Denoising and the Elucidation of Breathing Artefact

Figure 6E:
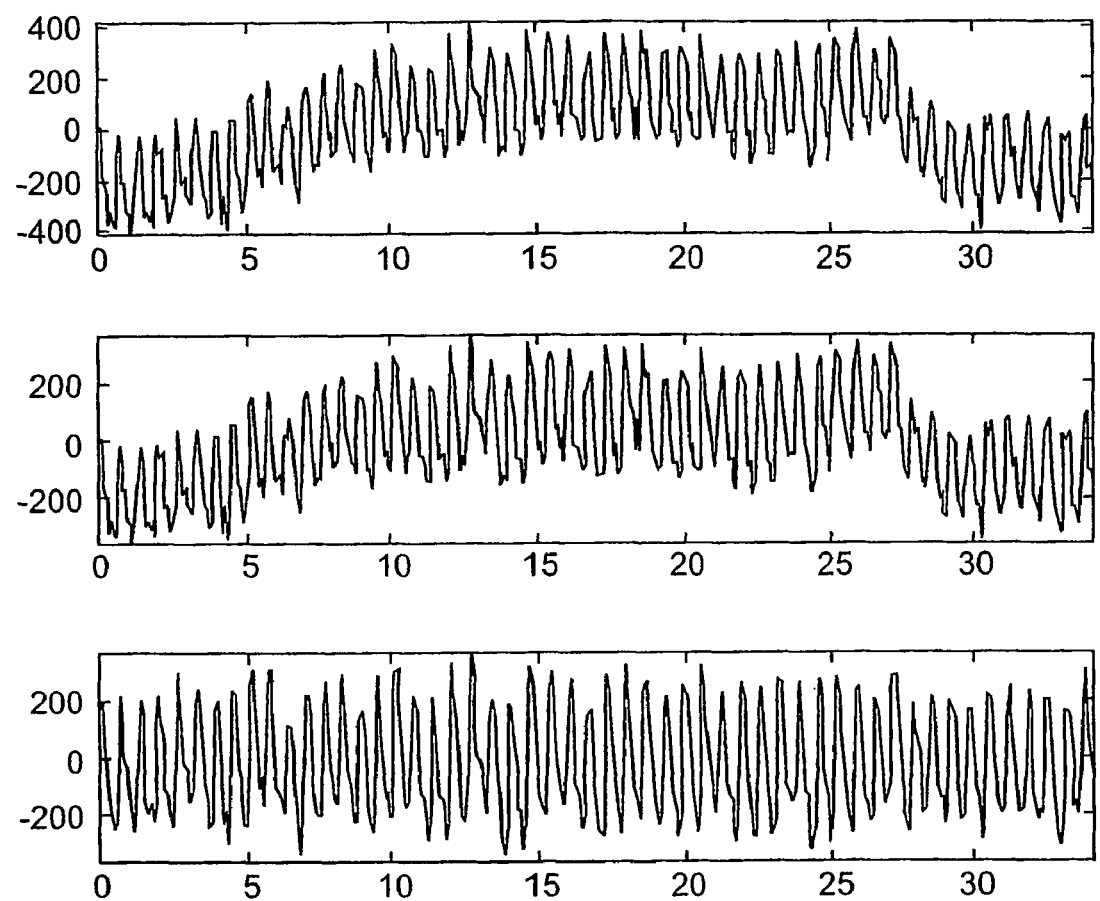

FIG. 6a shows a 35 second segment of pulse oximeter waveform. There is obvious drift in the signal. The corresponding scalogram and phase plots are given in FIGS. 6b and 6c respectively for a Morlet decomposition with $\omega_0=5.5$. FIGS. 6d and 6e illustrate a simple wavelet-based method for detrending and denoising the signal where the scalogram is essentially cropped, i.e. the high and low wavelet bandpass centre frequencies are set to zero. This removes both the very small and very large period fluctuations associated with noise and drift respectively. FIG. 6e shows, from top to bottom, the original signal, the reconstructed signal using all the scalogram information (a check) and the denoised and detrended signal reconstructed from the cropped scalogram in FIG. 6d. More advanced detrending and denoising includes filtering methodologies based on the wavelet transform modulus maxima and ridges, including methods to follow the ridges and other wavelet based features pertaining to the pulse and breathing signals through time.

FIG. 7 contains the decomposition of the same signal as that in FIG. 6, this time using a complete Morlet wavelet with $\omega_0=2$. The improved temporal isolation of the pulse features is apparent in the wavelet space scalogram of FIG. 7a. In addition, the phase plot of FIG. 7b shows a regular period oscillation at around 0.4 Hz particularly well. This, 2.5 second, periodicity corresponds to the regular breathing pattern of the patient—denoted as region B in the figure. In fact, we have separated the B–L region that was indicated in FIG. 5 into region B—breathing—and region L—other lower frequency signal components including drift. The denoising and detrending of the signal is carried out in the same way as in the previous figure to give the denoised and detrended signal shown in the lower plot of FIG. 7c. FIG. 7d shows a blow up of the first five seconds of the signals in FIG. 7c. The smoothing of the signal is obvious in the lower plot. The choice of the upper frequency cut-off is critical in partitioning relevant signal artefacts from noise. FIG. 7e shows three plots of the denoised and detrended signal where progressively higher cut-off thresholds have been used. This allows higher and higher frequency features back into the denoised signal.

More on the Elucidation of Breathing Artefact

Four, wavelet-based, methodologies may be employed for the monitoring of respiration and the extraction of the breathing rate from a standard pulse oximeter trace or photoplethysmograph (PPG) trace. These methodologies may be used independently, for example within an algorithm, or collectively using a polling mechanism. They are given as:

1. High Amplitude Banding.

When the breathing artefact is particularly pronounced, the breathing rate can be identified as a strong band or ridge of high transform values in the low (<1 Hz) frequency range. The arrow in FIG. 8(a) indicates one such ridge. In one preferred embodiment, this band can be identified by collapsing the scalogram down into two dimensions, as shown in FIG. 8(b). This is a wavelet based power spectrum: the summation of coefficients across scales factored by the reciprocal of the square of the scale value ($1/a^2$). The primary assumptions made in this methodology are: (1) the dominant features in the filtered trace are cardiac components and (2) the breathing rate is less than the heart rate. Alternative assumptions can also be employed according to the clinical situation, e.g. PPGs from neonates.

In another embodiment, the breathing ridge may be followed in wavelet space using standard ridge-following techniques. This allows sudden or short term changes in breathing rate to be identified and quantified in real time. Evidence for the applicability of this methodology is found in FIG. 9. Here a pulse oximeter trace, FIG. 9(a), is presented for a 60 second experiment. During the experiment the subject was instructed to half his breathing rate after 30 seconds. As can be seen in FIG. 9(b), a breathing ridge is clearly identifiable. This ridge drops in frequency (right hand horizontal scale) after 30 seconds. By identifying the phase of the wavelet transform along the ridge a clear indication of the timing of each breath can be determined—see FIG. 9(c).

2. Phase Methods.

As shown above, the phase of the wavelet coefficients can be used to identify the timing of each breath. However, cross-scale correlation of phase values, particularly for scalograms of low oscillation wavelets, can also be used as an indicator for low frequency, low amplitude, breathing features within the PPG trace.

In FIG. 10(a) a portion of the wavelet phase space scalogram is presented. As can be seen there is a very definite cross-scale correlation for the frequencies around the breathing rate—the dotted box (i.e. similar phase values are aligned vertically). By plotting the number of near zero modulus minima of the phase per scale against scale one can identify these areas of alignment as constant valued steps in the graph.

Figure 10B:
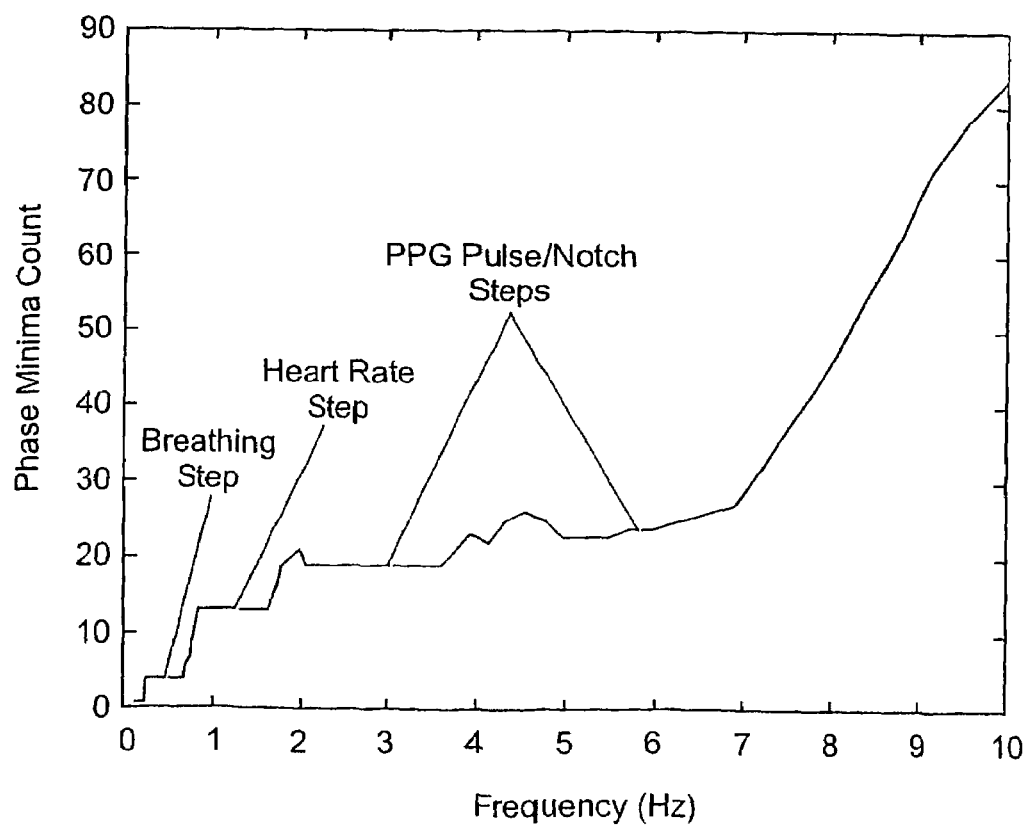

In the example of FIG. 10(b) the scale (horizontal) axis is presented as the band pass centre frequency of that scale. This diagram plots the count of phase modulus minima per scale against scale. This is indicative of the cross scale correlation in the wavelet phase space and can be used to associate regions of the scalogram with physiological features (e.g. breathing and heart rate). This diagram is the count of phase minima of the scalogram shown in FIG. 8.

As one can clearly see in this figure, the steps of constant phase count correlate extremely well with the wavelet spectrum peak positions of FIG. 8(b) (the spectrum of the same trace as that of FIG. 10(b)).

Note that the use of cross-correlation across scale can also be used to isolate individual features within the trace. See, for example, FIG. 16, where individual pulse features within the trace have been identified by finding the dominant frequency associated with the heart rate then following the points of equal phase up to higher frequencies. These techniques cannot be performed using conventional STFT methods where the temporal resolution at high frequencies is inferior and phase values are relative to the STFT frame origin rather than the wavelet centre.

3. Frequency Modulation.

Figure 11A:
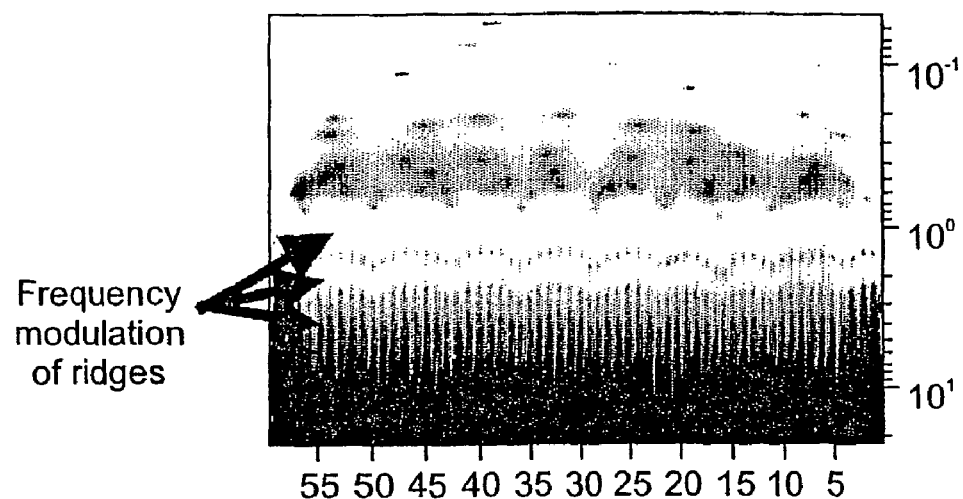

In some cases the amplitudes of the breathing related features within the PPG are such that they cannot easily be isolated as independent features within the transform space (e.g. they are of small amplitude, close to the dominant cardiac signal, etc). However, their effects on the dominant cardiac features can be observed. This is shown in FIG. 11(a) where the frequency of modulation corresponds to the breathing rate of the subject. Associated frequency of the cardiac features oscillate with a frequency identified as that of the breathing rate. This method cannot be utilised using standard Fourier techniques where temporal averaging reduces resolution in time so making identification of this modulation undetectable.

4. Amplitude Modulation.

Figure 11B:
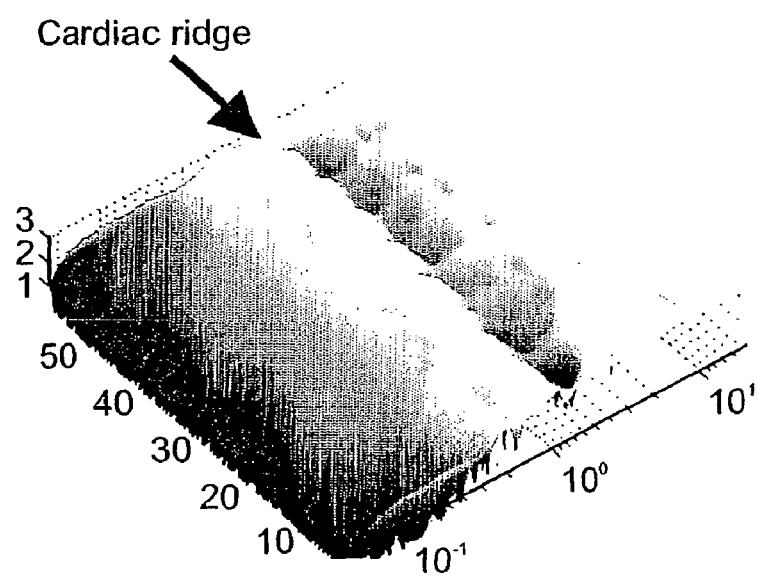
Figure 11C:
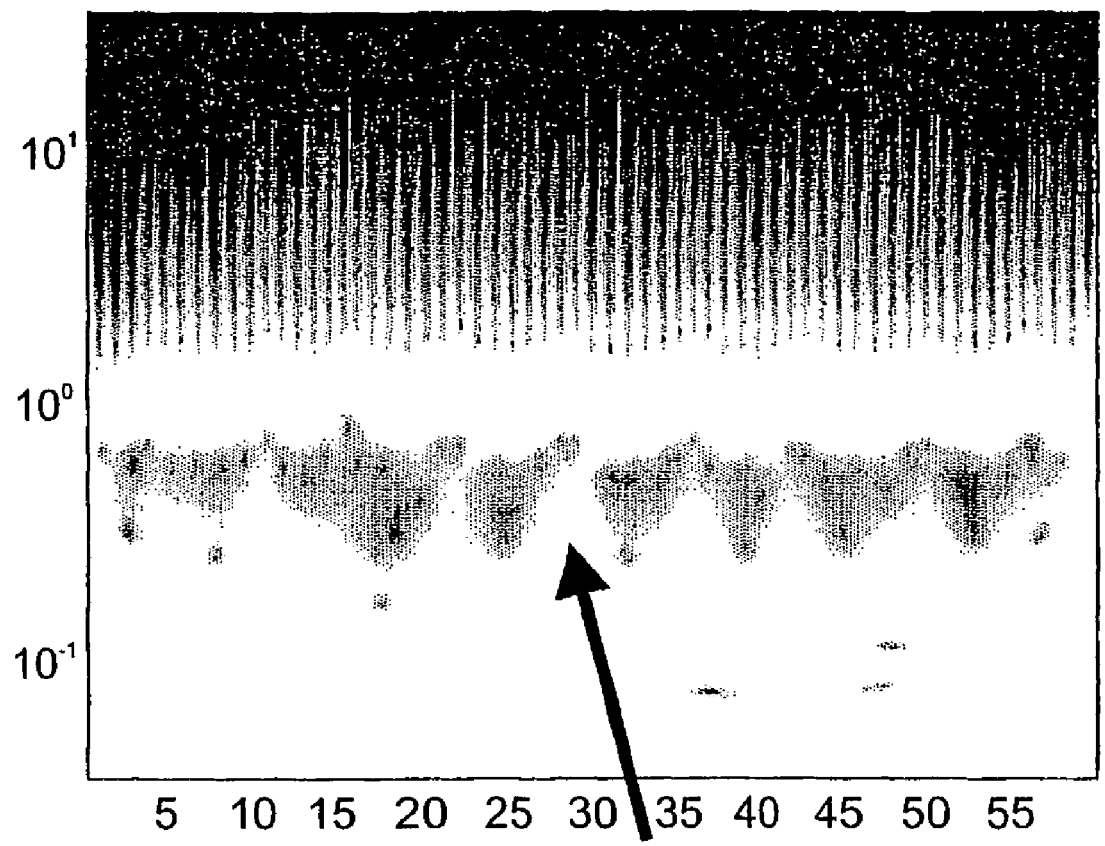

In some cases the amplitudes of the breathing related features within the PPG are such that they cannot easily be isolated as independent features within the transform space (e.g. they are of small amplitude, close to the dominant cardiac signal, etc). However, their effects on the dominant cardiac features can be observed. This is shown in FIG. 11(b) where the frequency of amplitude modulation corresponds to the breathing rate of the subject.

The amplitude dominant band corresponding to the cardiac features in wavelet space oscillates with a frequency identified as that of the breathing rate. Occasionally, when breaths are well separated individual breath features can be identified instead of a continuous, or modulated, band. This is particularly apparent when a low oscillation wavelet function is employed, as in FIG. 11(c). Again, this method cannot be utilised using standard Fourier techniques where temporal averaging reduces resolution in time so making identification of this modulation undetectable.

Wavelet Feature Analysis

A scheme is described for the analysis of features derived from statistical measures of the wavelet transformed signal at a given frequency level or by following a time-frequency feature in wavelet space—where the transform can be represented as the actual transform values, the modulus of transform values, the squared transform values (the scalogram) or some other simple transformation of the wavelet transform values. In the preferred embodiment these features derived from the wavelet transform at a selected frequency level may include the power, mean, skew, kurtosis and entropy. In addition, these may be found for the peak frequency for each individual scalogram rather than a constant predefined frequency level, where peak frequency is defined as the frequency level containing the most power when integrated across the scalogram to produce a wavelet power spectrum. FIG. 12 shows a schematic of the wavelet transform scalogram and the wavelet power spectrum obtained from integration along the time domain at each frequency level. The selected frequency level across which the statistical measures are obtained is shown dashed in the scalogram plot.

The algorithm allows the analysis of segments of the pulse oximetry signals. The algorithm also allows the visual inspection of the feature scatter in parameter space. The feature scatter is then used as input to a classification method e.g. a Bayesian classifier or neural network.

FIG. 13 shows the scatter plot derived from a signal data set obtained from two groups of children. One of the groups comprised a number of 'controls' taken from healthy children and were of relatively short duration these are marked by a 'o' in the figure. The other group were acquired from admitted patients attending the accident and emergency department of a UK children's hospital. Trace segments were selected from a PPG signal from each child and then decomposed using a wavelet transform. The feature distribution within the resulting scalograms were then probed across levels. The graph in FIG. 13 has been plotted with a logarithmic vertical axis to better separate the feature points in parameter space. This scaling is optional and linear scaling may better suit other chosen features. We can see from visual inspection that the controls are well separated from the admitted patients. The dashed line in the plot has been added for illustration and represents a possible separation line for dividing the two-dimensional data set into two classes.

Figure 14A:
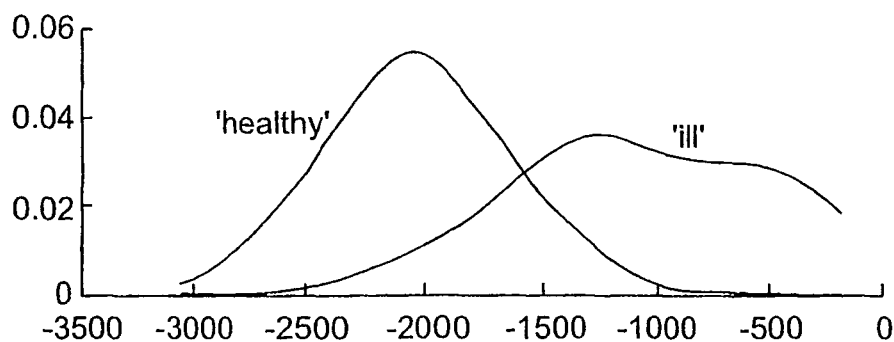
Figure 14B:
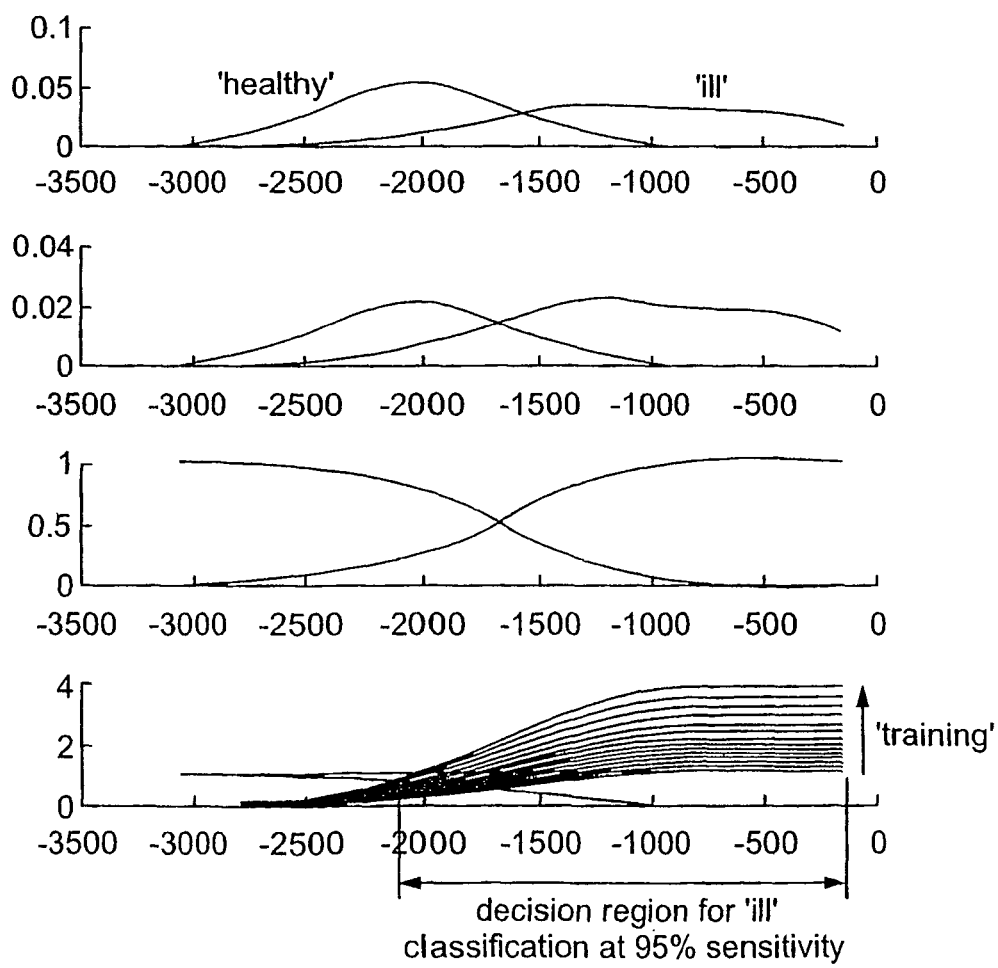
Figure 15:
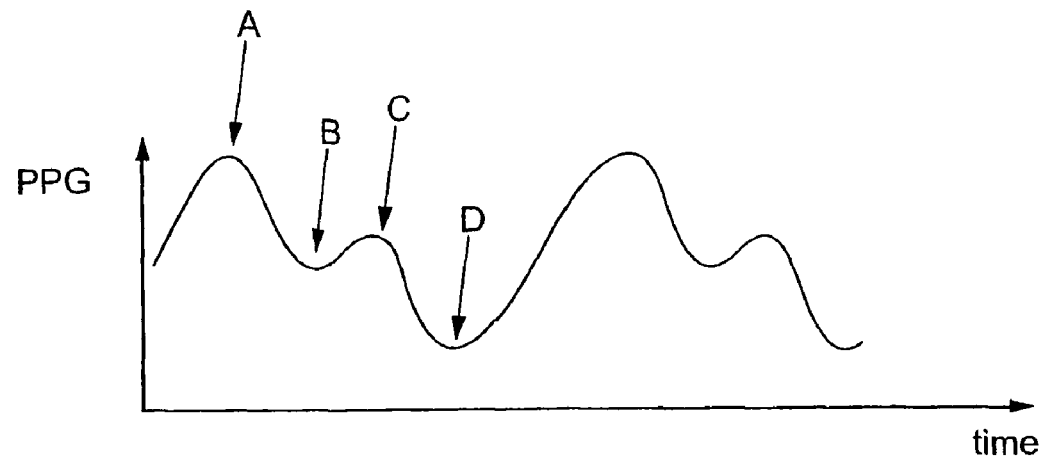
Figure 15:
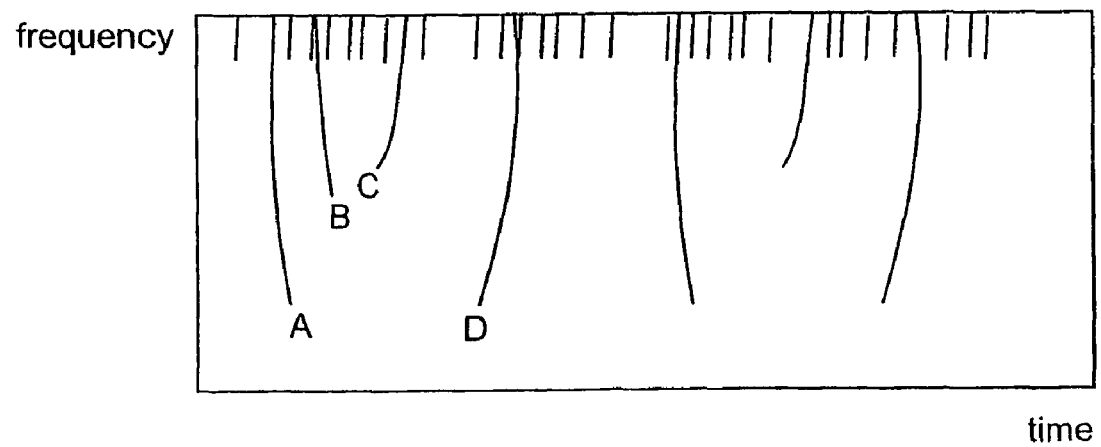

In order to determine from a data set which illness severity the patient belongs to a Bayesian or other classification method may be employed. FIG. 14 shows an example of the Bayesian classifier for the 'ill' and 'healthy' entropy data sets which gives a specificity of 84% and sensitivity of 81% for the determination of an 'ill' patient from a data sample. FIG. 14(a) shows smoothed data PDF's (Probability Density Functions) corresponding to the Entropy data given by the horizontal axis of FIG. 13. In FIG. 14(b) Top plot: smoothed PDF's, Second top plot: smoothed PDF's weighted according to class prevalence, Second bottom plot: probability of observation stemming from class 'healthy' or 'ill', Bottom plot: the classifier training towards a 95% sensitivity for detecting 'ill' patients.

Note that the two data sets have been smoothed prior to the classification. The classifier may be trained using an iterative procedure and a risk matrix to enhance the sensitivity (say to 95% or above) at the expense of sensitivity. For example, for 96% sensitivity, a specificity of only 43% is attained for the entropy data set produce (lowest plot of FIG. 14b).

Combinations of feature vectors can produce enhanced specificity-sensitivity values but with the requirement of increased computational effort. FIG. 13 contained a two-dimensional feature set (of power and entropy). The increased computational effort arising from the use of multidimensional feature sets can be remedied somewhat by reducing the number of components using, for example, principal component analysis or linear discriminant analysis during the preprocessing stage.

The use of features derived from wavelet transform are useful as clinical markers of current state of the patient health as shown in the example. The same classification method may also be used as a predictor of the future state of the patient's health by correlating future outcomes with wavelet feature data.

The classification method may also be extended to include other clinical parameters including triage category, capillary refill time, white cell count, age, etc.

The classification method may also be extended to further partition the data according to patient 'illness severity', where the system is initially trained on illness severities determined using suitable criteria by a clinician.

Usefulness in the Measurement of Compliance etc.

The wavelet-based denoising and feature extraction described herein will allow for a more accurate analysis of the photoplethysmographic waveform when used in the measurement and monitoring of physiological parameters. An example of this is in the determination of arterial compliance using the shape of, and reference points within, the plethysmographic signal. Modulus maxima following can be used to determine the location and nature of pertinent characteristic points in the PPG, e.g. the beginning and end of the initial upslope of the PPG trace, maxima, minima, etc. This is shown schematically in FIG. 15. Example PPG reference points used in the determination of clinically useful parameters are shown A,B,C,D and can be identified in the modulus maxima plot. The maxima lines can be used to better identify the characteristic points from within the signal.

In FIG. 16 the lower plot shows the wavelet transform (filtered) trace with individually isolated features of the trace marked by vertical lines. Note these have been identified through cross scale correlation of phase. Note also that peaks and troughs have been differentiated through the phase value—near zero corresponding to peaks and near $\pm\pi$ corresponding to troughs.

Implementation

FIG. 17 illustrates schematically one system for implementing the method of the invention.

A pulse oximeter 10 of known type has a probe 12 for obtaining readings from the finger, ear lobe or other suitable part of a patient. The pulse oximeter outputs a raw PPG signal to a computer 14 which carries out the wavelet transforms and associated analysis as discussed above. The computer 14 can output both the raw PPG signal and the results of processing the PPG signal to a VDU 16 and/or provide an output in the form of data at 18. The data output 18 may be in the form of a link to a remote location, a data carrier such as a disc or tape, or any other suitable format.

The mathematics of wavelet transforms are well described in the literature and known to those of ordinary skill in the art, and are not further described herein.

The immediately convenient manner of implementing the present invention is by connecting a computer to an existing pulse oximeter, as shown in FIG. 17. It will be readily apparent, however, that the invention could equally well be implemented by combining a pulse oximeter with suitable computational resources within a single, stand-alone instrument; or by passing the PPG signal from a conventional pulse oximeter over a data communications link to a remote computer which could be shared with other users.

The invention claimed is:

1. A method of measuring physiological parameters, comprising the steps of:
    using a pulse oximeter to obtain a pulse oximetry signal;
    decomposing the pulse oximetry signal by wavelet transform analysis;
    deriving a continuous wavelet transform surface:
plotting the surface against a location parameter and a scale parameter; and
following a feature on the plotted surface to derive one or more physiological parameters.

2. A method according to claim 1, in which the pulse oximetry signal is a photoplethysmogram (PPG).

3. A method as claimed in claim 1, in which the step of deriving a continuous wavelet transform surface comprises deriving the wavelet energy surfaces of the pulse oximeter signal.

4. A method as claimed in claim 1, in which the step of deriving a continuous wavelet transform surface includes the step of deriving the wavelet transform modulus of the pulse oximeter signal.

5. A method as claimed in claim 1, in which the scale parameter is a characteristic frequency of the wavelet used in the decomposition.

6. A method as claimed in claim 1, in which the scale parameter is the wavelet dilation.

7. A method as claimed in claim 1, including visually displaying information derived from the pulse oximetry signal by the wavelet transform analysis.

8. A method as claimed in claim 7, in which said information is displayed in real time.

9. A method as claimed in claim 7, in which said information includes one or more of: the distribution of energies within the pulse oximetry signal, coherent structures in the processed signal, a contour plot of the decomposed waveform, a surface plot of the decomposed waveform, and a 2D or 3D energy scalogram.

10. A method according to claim 7, in which the unprocessed pulse oximetry signal is also displayed.

11. A method according to claim 1, in which the step of following a feature on the plotted surface comprises identifying a ridge caused by respiration, and following said ridge to derive information relating to respiration.

12. A method according to claim 11, in which respiration information is derived from high amplitude ridges using ridge-following methods.

13. A method according to claim 11, in which the respiration information is derived by analysis of amplitude or frequency modulation.

14. A method according to claim 11, in which the information relating to respiration comprises a breathing rate.

15. A method according to claim 14, in which respiration information is derived from high amplitude ridges using ridge-following methods.

16. A method according to claim 14, in which the respiration information is derived by analysis of amplitude or frequency modulation.

17. A method according to claim 11, wherein said ridge following comprises the step of extracting phase information along the ridge to identify and/or analyze individual breaths.

18. A method according to claim 17, in which the respiration information is derived by cross scale correlation of phase values.

19. A method according to claim 1, in which decomposing the pulse oximetry signal is effective to remove, at least one of noise, artefact, and transient features.

20. A method according to claim 19, in which said removal employs inverse transformation of the cropped transform.

21. A method according to claim 19, in which said removal employs wavelet ridge methods.

22. A method according to claim 19, in which said removal employs modulus maxima methods.

23. A method according to claim 1, in which information from the transform is used to determine the present or predicted severity of illness of a subject.

24. A method according to claim 23, in which said information from the transform comprises features derived from the wavelet transform at a selected frequency level, and wherein said features are used as an input to a classification algorithm for the determination of the present or predicted severity of illness of a subject.

25. A method according to claim 24, wherein the features comprise at least one from the group including power, mean, skew, kurtosis and entropy.

26. A method according to claim 1, wherein the step of following a feature on the plotted surface comprises following the loci of maxima and/or minima of features on the surface.

27. A method according to claim 26, wherein the step of following the loci of maxima and/or minima of features on the surface comprises a ridge following technique.

28. A method according to claim 26, wherein the step of following the loci of maxima and/or minima of features on the surface comprises a modulus maxima technique.

29. A method according to claim 1, comprising the steps of identifying modulus maxima on the transform surface, using the modulus maxima following to determine the location and nature of pertinent points in the PPG, and determining a subject's arterial compliance based on the pertinent points.

30. A physiological measurement system comprising: a pulse oximeter which includes an optical probe and circuit means connected to the probe to derive a pulse oximetry signal from a subject when the probe is applied to the subject, and signal processing means arranged to:
receive the pulse oximetry signal;
decompose the pulse oximetry signal by wavelet transform analysis, said wavelet transform analysis employing a continuous wavelet function;
derive a wavelet time-scale energy surface;
plot the surface against a location parameter and a scale parameter; and
follow a feature on the plotted surface to derive one or more physiological parameters.

31. A system according to claim 30, further including a visual display unit operable to display the pulse oximetry signal and information derived therefrom in real time.

32. A method of measuring physiological parameters, comprising the steps of:
using a pulse oximeter to obtain a pulse oximetry signal;
decomposing the pulse oximetry signal by wavelet transform analysis;
deriving a continuous wavelet transform surface;
plotting the surface against a location parameter and a scale parameter;
identifying one or more ridges caused by respiration, then:
(a) identifying and following high amplitude ridges;
(b) extracting phase information from along the ridge;
(c) analyzing amplitude modulation;
(d) analyzing frequency modulation; and
(e) deriving information relating to respiration by polling between the results of methods (a) to(d).

33. The method of claim 32, in which the information relating to respiration comprises a breathing rate.

34. The method of claim 32, in which the information relating to respiration comprises the identification and/or analysis of individual breaths.

35. The method of claim 32, wherein the information relating to respiration is derived by cross scale correlation of phase values.

* * * * *